United States Patent
Yamamoto et al.

(10) Patent No.: US 10,064,760 B2
(45) Date of Patent: Sep. 4, 2018

(54) MANUFACTURING APPARATUS AND MANUFACTURING METHOD FOR MANUFACTURING ABSORBENT ARTICLE

(71) Applicant: Unicharm Corporation, Ehime (JP)

(72) Inventors: Hiroki Yamamoto, Kagawa (JP); Yoshihiko Matsumoto, Kagawa (JP)

(73) Assignee: Unicharm Corporation, Ehime (JP)

( * ) Notice: Subject to any disclaimer, the term of this patent is extended or adjusted under 35 U.S.C. 154(b) by 164 days.

(21) Appl. No.: 15/128,553

(22) PCT Filed: Oct. 16, 2014

(86) PCT No.: PCT/JP2014/077494
§ 371 (c)(1),
(2) Date: Sep. 23, 2016

(87) PCT Pub. No.: WO2015/145839
PCT Pub. Date: Oct. 1, 2015

(65) Prior Publication Data
US 2018/0168886 A1 Jun. 21, 2018

(30) Foreign Application Priority Data
Mar. 27, 2014 (JP) .................................. 2014-065255

(51) Int. Cl.
*A61F 13/00* (2006.01)
*A61F 13/15* (2006.01)
*A61F 13/496* (2006.01)

(52) U.S. Cl.
CPC .. *A61F 13/15747* (2013.01); *A61F 13/15585* (2013.01); *A61F 13/15723* (2013.01);
(Continued)

(58) Field of Classification Search
CPC .......... A61F 13/00; A61F 13/10; A61F 13/15; A61F 13/15; A61F 13/157; A61F 13/157;
(Continued)

(56) References Cited

U.S. PATENT DOCUMENTS 6,732,778 B1  5/2004  Machida et al.
8,168,254 B2  5/2012  Dovertie et al.

FOREIGN PATENT DOCUMENTS

JP  2002-035027 A  2/2002
JP  2009-535617 A  2/2002
(Continued)

OTHER PUBLICATIONS

International Search Report from corresponding PCT application No. PCT/JP2014/077494 dated Jan. 6, 2015 (4 pgs).
(Continued)

*Primary Examiner* — Jacob T Minskey
*Assistant Examiner* — Matthew Hoover
(74) *Attorney, Agent, or Firm* — Brinks Gilson & Lione

(57) ABSTRACT

A manufacturing apparatus for manufacturing an absorbent article, the manufacturing apparatus including: an upstream transport mechanism and a downstream transport mechanism that transports a stretchable sheet-like member along a transporting direction, the stretchable sheet-like member continuing along the transporting direction; an extension-ratio adjustment mechanism that is located between the upstream transport mechanism and the downstream transport mechanism, and that adjusts an extension ratio at which the stretchable sheet-like member extends in the transporting direction; and a processing apparatus that performs the certain process to the stretchable sheet-like member that is being transported by the downstream transport mechanism. When the upstream transport mechanism transports a first stretchable sheet-like member in which parts to be the
(Continued)

absorbent article are lined up at a first pitch in the transporting direction, the extension-ratio adjustment mechanism adjusts an extension ratio of the first stretchable sheet-like member so that the parts to be the absorbent article are lined up at a predetermined pitch. When the upstream transport mechanism transports a second stretchable sheet-like member in which the parts to be the absorbent article are lined up at a second pitch in the transporting direction, the second pitch being different from the first pitch, the extension-ratio adjustment mechanism adjusts an extension ratio of the second stretchable sheet-like member so that the parts to be the absorbent article are lined up at the predetermined pitch.

20 Claims, 10 Drawing Sheets

(52) U.S. Cl.
CPC .. *A61F 13/15764* (2013.01); *A61F 13/15772* (2013.01); *A61F 13/496* (2013.01); *A61F 2013/15821* (2013.01); *B65H 2801/57* (2013.01)

(58) Field of Classification Search
CPC .............. A61F 13/1574; A61F 13/1574; A61F 13/15747; A61F 13/155; A61F 13/155; A61F 13/1558; A61F 13/1558; A61F 13/15585; A61F 13/1572; A61F 13/1572; A61F 13/15723; A61F 13/1576; A61F 13/1576; A61F 13/15764; A61F 13/1577; A61F 13/1577; A61F 13/15772
See application file for complete search history.

(56) References Cited

FOREIGN PATENT DOCUMENTS

| | | |
|---|---|---|
| JP | 2003-521339 A | 7/2003 |
| JP | 2004-016611 A | 1/2004 |
| JP | 2005-080827 A | 3/2005 |
| JP | 2007-105453 A | 4/2007 |

OTHER PUBLICATIONS

International Preliminary Report on Patentability and Written Opinion from corresponding PCT application No. PcT/JP2014/077494 dated Oct. 6, 2016 (6 pgs).
European extended Search Report from corresponding European application No. 14887206.2 dated Feb. 21, 2017 (7 pgs).

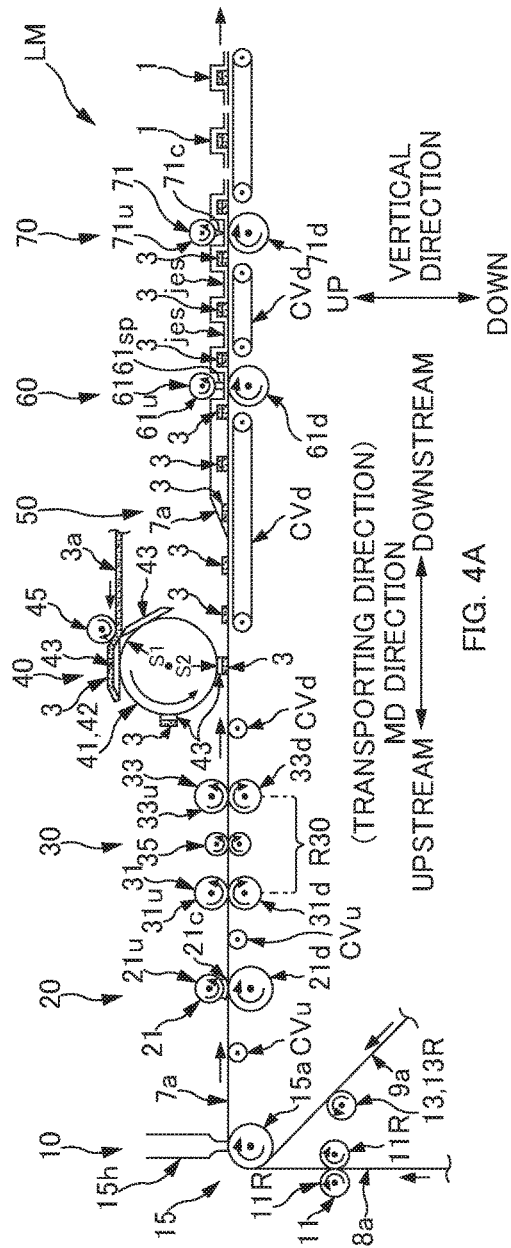
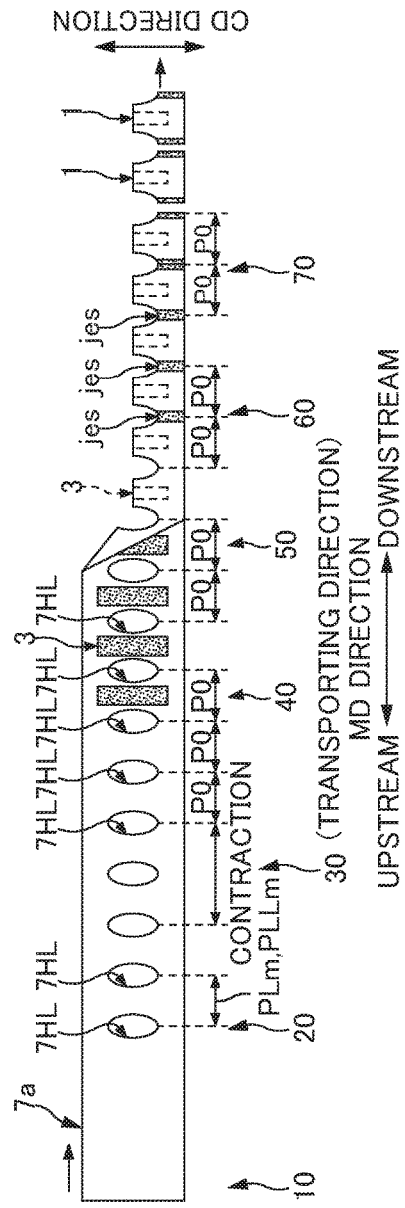
FIG. 4A
FIG. 4B

VIEW ALONG LINE B-B

MANUFACTURING APPARATUS AND MANUFACTURING METHOD FOR MANUFACTURING ABSORBENT ARTICLE

RELATED APPLICATION

The present application is a 35 U.S.C. § 371 national stage filing of International Patent Application No. PCT/JP2014/077494, filed Oct. 16, 2014, to which priority is claimed under 35 U.S.C. § 120 and through which priority is claimed under 35 U.S.C. § 119 to Japanese Priority Patent Application No. 2014-065255, filed Mar. 27, 2014, the entire disclosure of which is hereby incorporated by reference.

TECHNICAL FIELD

The invention relates to a manufacturing apparatus and a manufacturing method for an absorbent article such as a disposable diaper.

BACKGROUND ART

In a manufacturing line of a disposable diaper, which is an example of an absorbent article, a stretchable sheet-like member extends in the transporting direction and is being transported. And, the stretchable sheet-like member sequentially undergoes suitable processes such as attaching an absorbent main body which absorbs liquid, and is finally cut out on product-by-product basis, to produce the diaper. Accompanying with the cutting, the extended state of the stretchable sheet-like member is released and contracts in the transporting direction. Then, the exterior of the diaper, which is mainly composed of the stretchable sheet-like member, contracts, and the diapers which have been contracted in the foregoing manner are marketed. Accordingly, the diaper in a stretchable state is used by a user (e.g. a wearer).

CITATION LIST

Patent Literature

[Patent Literature 1] Japanese Unexamined Patent Application Publication No. 2007-105453

SUMMARY OF INVENTION

Technical Problem

In some manufacturing lines of diapers, the diapers whose sizes are different (e.g. L-size diapers or S-size diapers) are manufactured. In this case, a product pitch on the stretchable sheet-like member differs per the size of a product; that is, a pitch at which parts to be a diaper are lined up in the transporting direction on the sheet-like member differs per the size of a product. For example, a sheet-like member for L-size diapers has a large pitch is, and a sheet-like member for S-size diapers has a small pitch. Accordingly, various processing apparatuses included in the manufacturing line are each required to have a configuration which can support alteration of its product pitch.

For example, a common cutter apparatus, which is an example of the processing apparatuses, has a cutter roll which rotates. On the outer circumferential surface of the roll, cutter blades serving as processing portions are provided at an arrangement pitch in the rotating direction, the arrangement pitch being substantially equal to the product pitch. In this cases, in order to support alteration of the foregoing product pitch, the cutter apparatus needs to have a plurality of cutter rolls whose cutter blades have different arrangement pitch from each other. In such a configuration, every time when changing the product size, it is necessary to replace and install a cutter roll for the intended-size diapers, in the manufacturing line. This causes not only a problem of facilities-cost increase, and also causes a problem of decrease of capacity utilization.

In this regard, if the processing apparatus can be shared, the foregoing problem can be avoided, and cost reduction and productivity improvement can be achieved regardless of the product size of a diaper.

The invention has been made in view of the above problems, and an advantage thereof is to share processing apparatuses each of which performs a process to a stretchable sheet-like member associated with manufacturing an absorbent article, regardless of the size of the absorbent article to be manufactured.

Solution to Problem

An aspect of the invention to achieve the above advantage is a manufacturing apparatus for manufacturing the absorbent article by performing a certain process to a stretchable sheet-like member associated with the absorbent article,
  the stretchable sheet-like member continuing along a transporting direction,
  the apparatus including:
  an upstream transport mechanism that transports the stretchable sheet-like member along the transporting direction;
  a downstream transport mechanism
    that is located downstream in the transporting direction from the upstream transport mechanism, and
    that transports the stretchable sheet-like member along the transporting direction;
  an extension-ratio adjustment mechanism
    that is located between the upstream transport mechanism and the downstream transport mechanism, and
    that adjusts an extension ratio at which the stretchable sheet-like member extends in the transporting direction; and
  a processing apparatus that performs the certain process to the stretchable sheet-like member that is being transported by the downstream transport mechanism,
  when the upstream transport mechanism transports a first stretchable sheet-like member in which parts to be the absorbent article are lined up at a first pitch in the transporting direction,
    the extension-ratio adjustment mechanism adjusting an extension ratio of the first stretchable sheet-like member so that the parts to be the absorbent article are lined up at a predetermined pitch, and
    the extension-ratio adjustment mechanism transferring the first stretchable sheet-like member to the downstream transport mechanism, and
  when the upstream transport mechanism transports a second stretchable sheet-like member in which the parts to be the absorbent article are lined up at a second pitch in the transporting direction, the second pitch being different from the first pitch,
    the extension-ratio adjustment mechanism adjusting an extension ratio of the second stretchable sheet-like member so that the parts to be the absorbent article are lined up at the predetermined pitch, and the extension-ratio adjustment mechanism transferring the second stretchable sheet-like member to the downstream transport mechanism.

Further, a manufacturing method for manufacturing an absorbent article by performing a certain process to a stretchable sheet-like member associated with the absorbent article,
the stretchable sheet-like member continuing along a transporting direction,
the method including:
transporting the stretchable sheet-like member by an upstream transport mechanism along the transporting direction;
transporting the stretchable sheet-like member by a downstream transport mechanism along the transporting direction,
the downstream transport mechanism being located downstream in the transporting direction from the upstream transport mechanism;
adjusting by an extension-ratio adjustment mechanism an extension ratio at which the stretchable sheet-like member extends in the transporting direction,
the extension-ratio adjustment mechanism being located between the upstream transport mechanism and the downstream transport mechanism; and
performing the certain process by a processing apparatus to the stretchable sheet-like member that is being transported by the downstream transport mechanism, wherein
when the upstream transport mechanism transports a first stretchable sheet-like member in which parts to be the absorbent article are lined up at a first pitch in the transporting direction,
in the adjusting, an extension ratio of the first stretchable sheet-like member is adjusted sot that the parts to be the absorbent article are lined up at a predetermined pitch, and
the first stretchable sheet-like member is transferred to the downstream transport mechanism, and
when the upstream transport mechanism transports a second stretchable sheet-like member in which parts to be the absorbent article are lined up at a second pitch in the transporting direction, the second pitch being different from the first pitch,
in the adjusting, an extension ratio of the second stretchable sheet-like member is adjusted sot that the parts to be the absorbent article are lined up at the predetermined pitch, and
the second stretchable sheet-like member is transferred to the downstream transport mechanism.

Other features of this invention will become apparent from the description in this specification and the attached drawings.

Advantageous Effects of Invention

According to the invention, it is possible to share a processing apparatus which performs a process to a stretchable sheet-like member relating to manufacturing of an absorbent article, regardless of the size of the absorbent article to be manufactured.

BRIEF DESCRIPTION OF DRAWINGS

FIG. 4A is a schematic side view of a manufacturing line LM of a diaper 1 according to the present embodiment, and FIG. 4B is a schematic plan view showing how diapers 1 are manufactured.

DESCRIPTION OF EMBODIMENTS

Figure 1A:
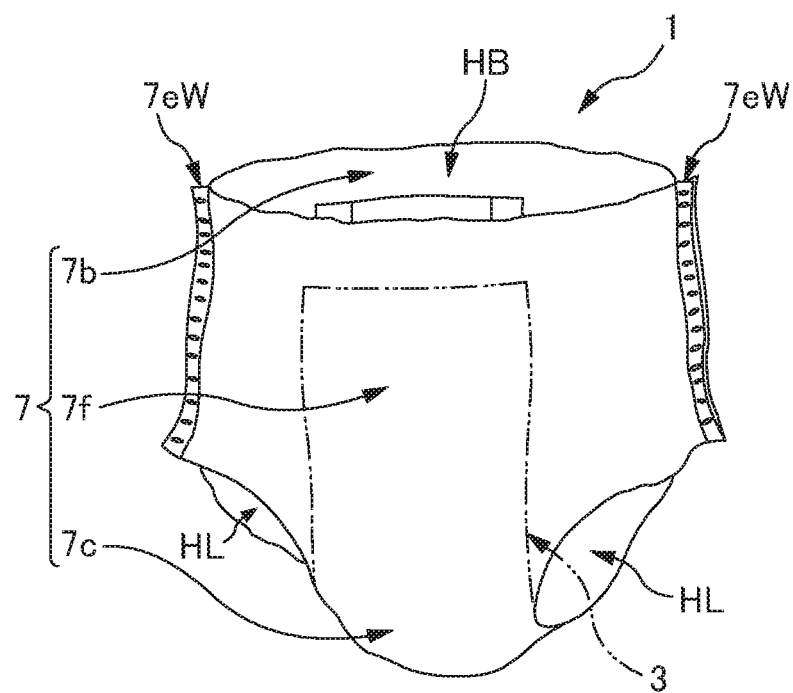
FIG. 1A is a schematic perspective view of a pull-on diaper 1 exemplifying an absorbent article according to the present embodiment.

At least the following matters will be made clear by the description in the present specification and the accompanying drawings.

A manufacturing apparatus for manufacturing an absorbent article by performing a certain process to a stretchable sheet-like member associated with the absorbent article,
the stretchable sheet-like member continuing along a transporting direction,
the apparatus including:
an upstream transport mechanism that transports the stretchable sheet-like member along the transporting direction;
a downstream transport mechanism
that is located downstream in the transporting direction from the upstream transport mechanism, and
that transports the stretchable sheet-like member along the transporting direction;
an extension-ratio adjustment mechanism
that is located between the upstream transport mechanism and the downstream transport mechanism, and
that adjusts an extension ratio at which the stretchable sheet-like member extends in the transporting direction; and
a processing apparatus that performs the certain process to the stretchable sheet-like member that is being transported by the downstream transport mechanism,
when the upstream transport mechanism transports a first stretchable sheet-like member in which parts to be the absorbent article are lined up at a first pitch in the transporting direction,
the extension-ratio adjustment mechanism adjusting an extension ratio of the first stretchable sheet-like member so that the parts to be the absorbent article are lined up at a predetermined pitch, and the extension-ratio adjustment mechanism transferring the first stretchable sheet-like member to the downstream transport mechanism, and when the upstream transport mechanism transports a second stretchable sheet-like member in which the parts to be the absorbent article are lined up at a second pitch in the transporting direction, the second pitch being different from the first pitch, the extension-ratio adjustment mechanism adjusting an extension ratio of the second stretchable sheet-like member so that the parts to be the absorbent article are lined up at the predetermined pitch, and the extension-ratio adjustment mechanism transferring the second stretchable sheet-like member to the downstream transport mechanism.

With such a manufacturing apparatus for an absorbent article, it is possible to share the processing apparatus which performs a process to the stretchable sheet-like member, regardless of the size of the absorbent article. The detail is as follow. Assuming that the first stretchable sheet-like member is prepared as a material of first-size absorbent articles, and that the second stretchable sheet-like member is prepared as a material of second-size absorbent articles, the second size being different from the first size. The upstream transport mechanism transports the first stretchable sheet-like member so that parts to be the absorbent article are lined up at the first pitch, and the upstream transport mechanism transports the second stretchable sheet-like member so that the parts to be the absorbent article are lined up at the second pitch. On the other hand, in the extension-ratio adjustment mechanism located between the upstream transport mechanism and the downstream transport mechanism, when the stretchable sheet-like member that is transported from the upstream transport mechanism along the transporting direction is the first stretchable sheet-like member, the extension ratio of the first stretchable sheet-like member is adjusted so that the parts to be the absorbent article are lined up at the predetermined pitch. Then, the first stretchable sheet-like member is transferred to the downstream transport mechanism. When the stretchable sheet-like member that is transported from the upstream transport mechanism along the transporting direction is the second stretchable sheet-like member, the extension ratio of the second stretchable sheet-like member is adjusted so that the parts to be the absorbent article are lined up at the predetermined pitch. Then, the second stretchable sheet-like member is transferred to the downstream transport mechanism. Accordingly, in both cases of the first stretchable sheet-like member and the second stretchable sheet-like member, it is sufficient that the processing apparatus performs the certain process at the predetermined pitch. This allows the first stretchable sheet-like member to undergo a process for first-size absorbent articles at a necessary pitch, and this also allows the second stretchable sheet-like member to undergo a process for second-size absorbent articles at a necessary pitch. This makes it possible to share the processing apparatus, regardless of the size of the absorbent article to be manufactured.

In such a manufacturing apparatus for an absorbent article, it is desirable that of the first stretchable sheet-like member and the second stretchable sheet-like member, to either one stretchable sheet-like member that is being transported by the downstream transport mechanism, the processing apparatus performs the certain process at the predetermined pitch.

With such a manufacturing apparatus for an absorbent article, a single processing apparatus is enough to perform the certain process at the predetermined pitch to both of the first and second stretchable sheet-like members. In other words, it is possible to share the processing apparatus which performs the certain process, regardless of the size of the absorbent article to be manufactured.

In such a manufacturing apparatus for an absorbent article, it is desirable that the processing apparatus attaches an absorbent main body to the stretchable sheet-like member at the predetermined pitch, the absorbent main body is a component that should be provided to each absorbent article and absorbs liquid, and the attaching is performed as the certain process.

With such a manufacturing apparatus for an absorbent article, a single processing apparatus is enough to allow the absorbent main body to be attached at the predetermined pitch to both of the first and second stretchable sheet-like members. In other words, it is possible to share the processing apparatus which attaches the absorbent main body, regardless of the size of the absorbent article to be manufactured.

In such a manufacturing apparatus for an absorbent article, it is desirable that before the stretchable sheet-like member is transported to the processing apparatus, the stretchable sheet-like member is two-folded in a CD direction intersecting the transporting direction, and in the processing apparatus, the stretchable sheet-like member is fixed in a state in which the stretchable sheet-like member is two-folded, the fixing being performed by forming joined parts at the predetermined pitch in the stretchable sheet-like member that has been two-folded, the forming being performed as the certain process.

With such a manufacturing apparatus for an absorbent article, a single processing apparatus is enough to allow the joined part to be formed at the predetermined pitch in both of the first and second stretchable sheet-like members. In other words, it is possible to share the processing apparatus which forms the joined parts, regardless of the size of the absorbent article to be manufactured.

In such a manufacturing apparatus for an absorbent article, it is desirable that before the stretchable sheet-like member is transported to the processing apparatus, the stretchable sheet-like member is two-folded in a CD direction intersecting the transporting direction, and is fixed in a state in which the stretchable sheet-like member is two-folded, and the processing apparatus produces the absorbent article, the producing being performed by cutting at the predetermined pitch the stretchable sheet-like member that has been two-folded, the cutting being performed as the certain process.

With such a manufacturing apparatus for an absorbent article, a single processing apparatus is enough to be able to cut at the predetermined pitch both of the first and second stretchable sheet-like members. In other words, it is possible to share the processing apparatus which performs the cutting, regardless of the size of the absorbent article to be manufactured.

In such a manufacturing apparatus for an absorbent article, it is desirable that of the first stretchable sheet-like member and the second stretchable sheet-like member, either one stretchable sheet-like member that is being transported by the upstream transport mechanism is in a state in which the stretchable sheet-like member extends in the transporting direction, the manufacturing apparatus further comprises a reference-section forming apparatus that forms a physical reference section in the stretchable sheet-like member, the stretchable sheet-like member being in the extending state and being transported by the upstream transport mechanism, the extension-ratio adjustment mechanism includes:

a transport path in which the stretchable sheet-like member is transported;

a sensor
that detects the reference section after the extension ratio has been adjusted in the extension-ratio adjustment mechanism and
that outputs a detection signal; and a transportation-state alteration device that alters a transportation state of the stretchable sheet-like member in the transport path so that a position in the stretchable sheet-like member for the certain process is located close to a target position for the certain process,
the alteration being performed according to the detection signal of the sensor.

With such a manufacturing apparatus for an absorbent article, the reference section is formed in the stretchable sheet-like member which is in the extending state. Accordingly, the reference section can be formed exactly at the target position in the stretchable sheet-like member. Consequently, the reference section can effectively function as a positional reference on the stretchable sheet-like member.

The sensor detects the reference section after the extension ratio has been adjusted in the extension-ratio adjustment mechanism, and outputs the detection signal. According to the detection signal, the transportation-state alteration device alters the transportation state of the stretchable sheet-like member in the transport path of the extension-ratio adjustment mechanism. Thereby, the stretchable sheet-like member is adjusted so that the position in the stretchable sheet-like member for the certain process is located close to the target position for the certain process. Accordingly, in the stretchable sheet-like member whose extension ratio has been adjusted so that the parts to be the absorbent article are lined up the predetermined pitch, the processing apparatus can perform the certain process precisely at the target position for the certain process.

In such a manufacturing apparatus for an absorbent article, it is desirable that the manufacturing apparatus further comprises:

a first reference-section forming apparatus that forms leg openings at the first pitch as the reference section in the first stretchable sheet-like member in which the parts to be the absorbent article are lined up at the first pitch in the transporting direction,
the leg openings being associated with the absorbent article; and a second reference-section forming apparatus that forms leg openings at the second pitch as the reference section in the second stretchable sheet-like member in which the parts to be the absorbent article are lined up at the second pitch in the transporting direction,
the leg openings being associated with the absorbent article.

With such a manufacturing apparatus for an absorbent article, in both of the first stretchable sheet-like member and the second stretchable sheet-like member, the leg opening is used as the reference section. Accordingly, other processes necessary to manufacture the absorbent article can be performed using the leg opening as a reference. This makes it possible to manufacture an absorbent article with which a wearer is less likely to feel uncomfortable.

In both of the first stretchable sheet-like member and the second stretchable sheet-like member, the leg opening serving as the reference section is formed for each part to be the absorbent article. Accordingly, the foregoing other processes can be performed precisely to each of the parts to be the absorbent article. This makes it possible to finish each absorbent article with higher precision.

In such a manufacturing apparatus for an absorbent article, it is desirable that the predetermined pitch is smaller than the first pitch and is smaller than the second pitch.

With such a manufacturing apparatus for an absorbent article, in both of the first stretchable sheet-like member and the second stretchable sheet-like member, the adjustment of the pitch to the predetermined pitch can be performed by means of contraction only. This makes it possible to anticipate and avoid a trouble such as breakage of the stretchable sheet-like member, which could be happen when the adjustment is performed by the extension. Consequently, the adjustment of the stretchable sheet-like member to the predetermined pitch is steady.

In such a manufacturing apparatus for an absorbent article, it is desirable that the manufacturing apparatus further comprises a plurality of mechanism units each of which is composed of the extension-ratio adjustment mechanism and the downstream transport mechanism, the plurality of mechanism units being lined up in the transporting direction, and the predetermined pitch is different between at least two mechanism units of the plurality of mechanism units.

With such a manufacturing apparatus for an absorbent article, the predetermined pitch is different between a processing apparatus included in the downstream transport mechanism of one of the two mechanism units and a processing apparatus included in the downstream transport mechanism of the other mechanism unit. This makes it possible to individually adjust the predetermined pitch. Consequently, these two processing apparatuses can perform their own processes to both of the first stretchable sheet-like member and the second stretchable sheet-like member at pitches which is respectively most suitable to their own processes.

In such a manufacturing apparatus for an absorbent article, it is desirable that the manufacturing apparatus further comprises a plurality of mechanism units each of which is composed of the extension-ratio adjustment mechanism and the downstream transport mechanism, the plurality of mechanism units being lined up in the transporting direction, and the predetermined pitches of all of the plurality of mechanism units are identical.

With such a manufacturing apparatus for an absorbent article, the extension-ratio adjustment mechanism of each of the plurality of mechanism units adjusts the stretchable sheet-like member so that the predetermined pitches of all of the plurality of mechanism units are identical. That is, at each time immediately before the processing apparatuses of the mechanism units, the stretchable sheet-like member is securely adjusted so that the parts to be the absorbent article are lined up at the equal predetermined pitch. Each processing apparatus can perform its own process at the predetermined pitch to the first stretchable sheet-like member and the second stretchable sheet-like member which have undergone the adjustment. Consequently, each processing apparatus of each mechanism units can perform its own processes to the stretchable sheet-like member with high positioning accuracy.

Further,
a manufacturing method for manufacturing an absorbent article by performing a certain process to a stretchable sheet-like member associated with the absorbent article,
the stretchable sheet-like member continuing along a transporting direction,
the method including:
transporting the stretchable sheet-like member by an upstream transport mechanism along the transporting direction;
transporting the stretchable sheet-like member by a downstream transport mechanism along the transporting direction,
the downstream transport mechanism being located downstream in the transporting direction from the upstream transport mechanism;
adjusting by an extension-ratio adjustment mechanism an extension ratio at which the stretchable sheet-like member extends in the transporting direction,
the extension-ratio adjustment mechanism being located between the upstream transport mechanism and the downstream transport mechanism; and
performing the certain process by a processing apparatus to the stretchable sheet-like member that is being transported by the downstream transport mechanism, wherein
when the upstream transport mechanism transports a first stretchable sheet-like member in which parts to be the absorbent article are lined up at a first pitch in the transporting direction,
in the adjusting, an extension ratio of the first stretchable sheet-like member is adjusted sot that the parts to be the absorbent article are lined up at a predetermined pitch, and
the first stretchable sheet-like member is transferred to the downstream transport mechanism, and
when the upstream transport mechanism transports a second stretchable sheet-like member in which parts to be the absorbent article are lined up at a second pitch in the transporting direction, the second pitch being different from the first pitch,
in the adjusting, an extension ratio of the second stretchable sheet-like member is adjusted sot that the parts to be the absorbent article are lined up at the predetermined pitch, and
the second stretchable sheet-like member is transferred to the downstream transport mechanism.

With such a manufacturing method for an absorbent article, it is possible to share the processing apparatus which performs a process to the stretchable sheet-like member, regardless of the size of the absorbent article. The detail is as follow. Assuming that the first stretchable sheet-like member is prepared as a material of first-size absorbent articles, and that the second stretchable sheet-like member is prepared as a material of second-size absorbent articles, the second size being different from the first size. The upstream transport mechanism transports the first stretchable sheet-like member so that parts to be the absorbent article are lined up at the first pitch, and the upstream transport mechanism transports the second stretchable sheet-like member so that the parts to be the absorbent article are lined up at the second pitch. On the other hand, in the extension-ratio adjustment mechanism located between the upstream transport mechanism and the downstream transport mechanism, when the stretchable sheet-like member that is transported from the upstream transport mechanism along the transporting direction is the first stretchable sheet-like member, the extension ratio of the first stretchable sheet-like member is adjusted so that the parts to be the absorbent article are lined up at the predetermined pitch. Then, the first stretchable sheet-like member is transferred to the downstream transport mechanism. When the stretchable sheet-like member that is transported from the upstream transport mechanism along the transporting direction is the second stretchable sheet-like member, the extension ratio of the second stretchable sheet-like member is adjusted so that the parts to be the absorbent article are lined up at the predetermined pitch. Then, the second stretchable sheet-like member is transferred to the downstream transport mechanism. Accordingly, in both cases of the first stretchable sheet-like member and the second stretchable sheet-like member, it is sufficient that the processing apparatus performs the certain process at the predetermined pitch. This allows the first stretchable sheet-like member to undergo a process for first-size absorbent articles at a necessary pitch, and this also allows the second stretchable sheet-like member to undergo a process for second-size absorbent articles at a necessary pitch. This makes it possible to share the processing apparatus, regardless of the size of the absorbent article to be manufactured.

Present Embodiment

A manufacturing apparatus for an absorbent article according to the present embodiment is used in a manufacturing line LM of pull-on disposable diapers 1, which is an example of the absorbent article.

Figure 1B:
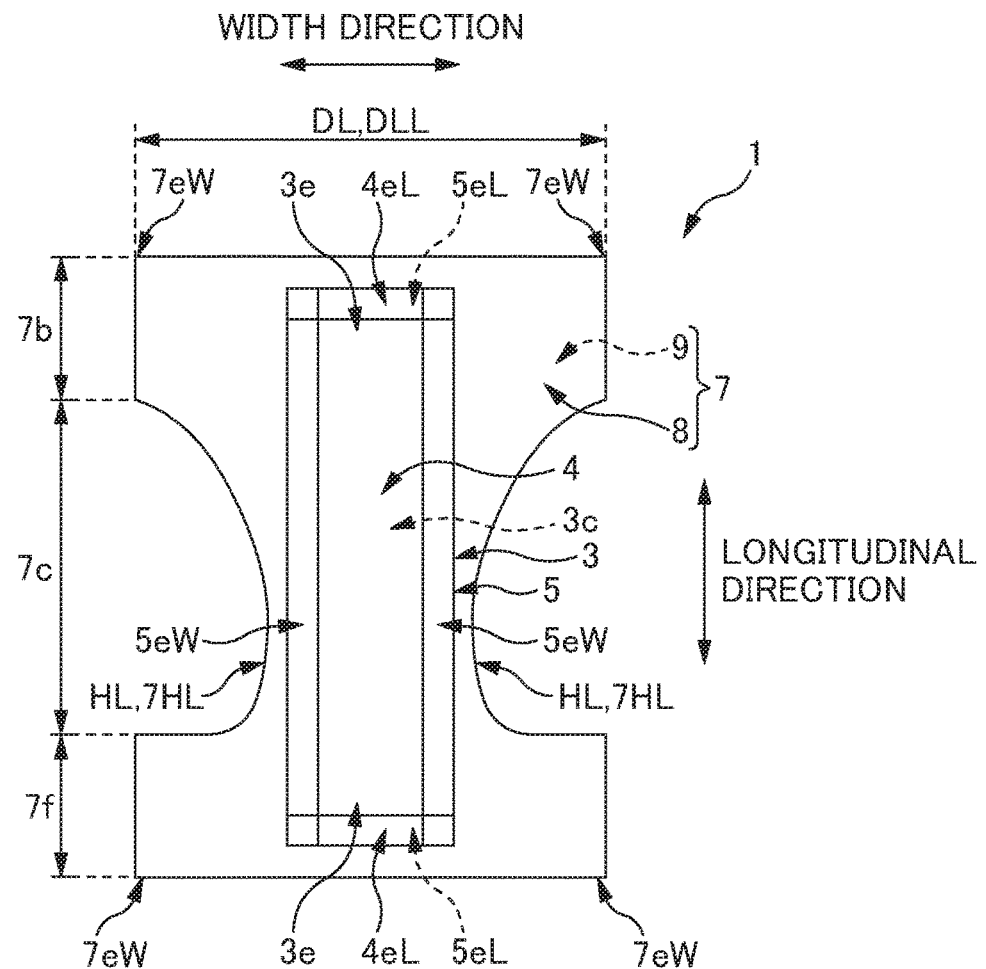
FIG. 1B is a schematic plan view of a diaper 1 which is spread out, as viewed from its skin side.
Figure 2:
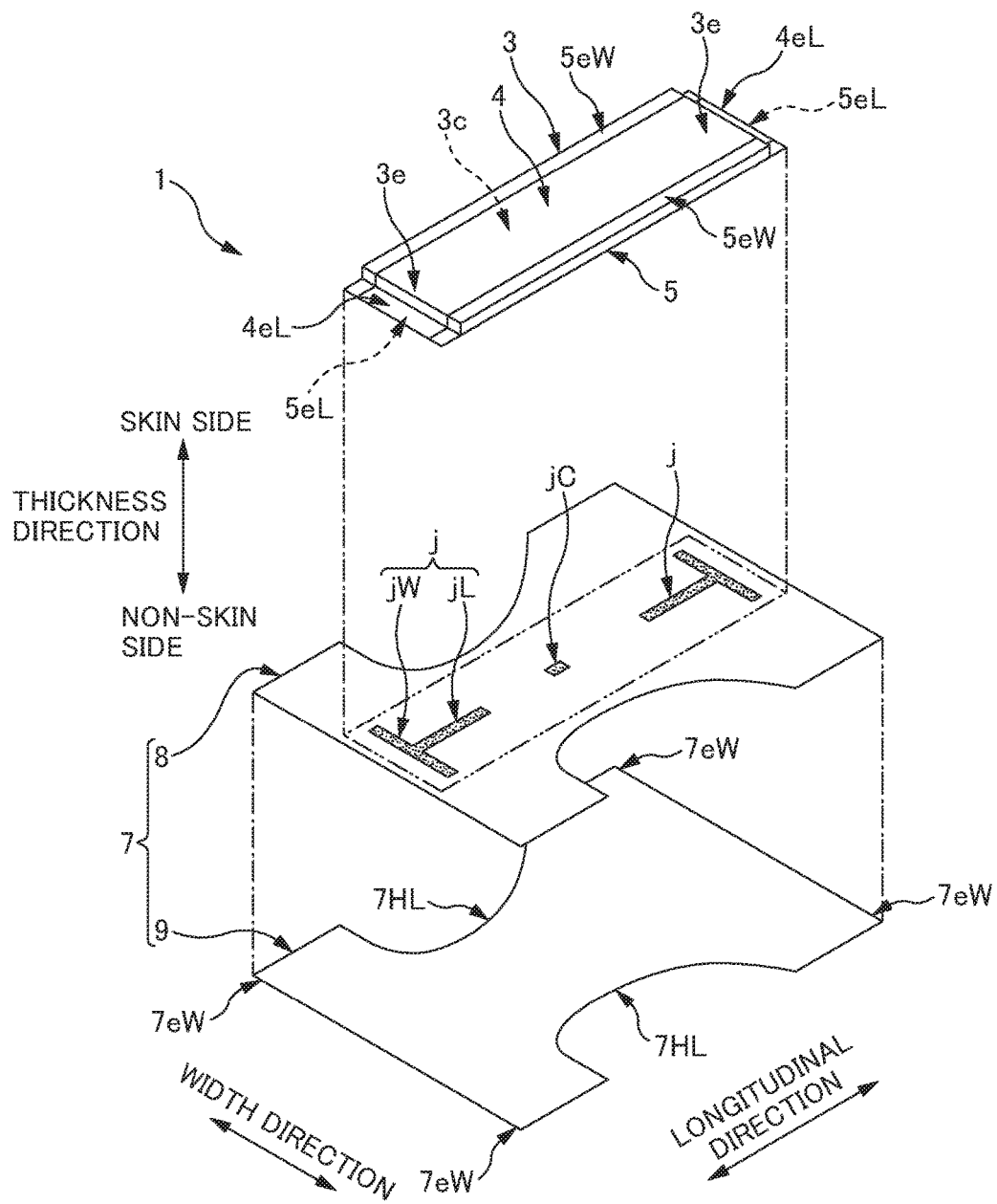
FIG. 2 is a schematic perspective view of the diaper 1 which is spread out and exploded.

FIG. 1A is a schematic perspective view of a pull-on diaper 1. FIG. 1B is a schematic plan view of the diaper 1 which is spread out, as viewed from its skin side. FIG. 2 is a schematic perspective view of the diaper 1 which is spread out and exploded.

In the description below, the side of a diaper 1 which should be located at the skin side of a wearer is merely referred to as a "skin side", and the side which should be located at the non-skin side of the wearer is merely referred to as a "non-skin side".

As shown in FIGS. 1B and 2, the diaper 1 is, for example, a diaper 1 consisting of two pieces. That is, the diaper 1 includes: an absorbent main body 3 in a substantially rectangular shape when viewed from above, as a first component, which absorbs excretion liquid such as urine; and an exterior sheet 7 in a substantially hourglass shape when viewed from above, as an second component, which covers the non-skin-side surface of the absorbent main body 3 and serves as an exterior of a diaper 1.

As shown in FIG. 2, the absorbent main body 3 includes an absorbent core 3c which absorbs excretion liquid. The absorbent core 3c is a body formed by shaping liquid-absorbent fiber (e.g. pulp fiber) or liquid-absorbent particles (e.g. superabsorbent polymer) into a predetermined shape (e.g. a substantially rectangular shape when viewed from above). Such an absorbent core 3c may be covered as necessary with a liquid-permeable cover sheet such as tissue paper.

On the skin-side surface of the absorbent core 3c, a liquid permeable top sheet 4 (e.g. nonwoven fabric) is provided so as to cover the surface. Also, on the non-skin-side surface of the absorbent core 3c, a liquid-impermeable leak-proof sheet 5 (e.g. film) is provided so as to cover the entire of the surface.

Here, in this example, both of the sheets 4 and 5 have a substantially rectangular shape when viewed from above, and extend and project outwardly from the longitudinal ends of the absorbent core 3c. The projecting parts 4eL of the top sheet 4 and the projecting parts 5eL of the leak-proof sheet 5 are respectively joined to each other by means such as adhesion or welding. In the width direction, the leak-proof sheet 5 extends and projects outwardly from both ends of the absorbent core 3c. These projecting parts 5eW and 5eW are folded back to the skin side, and are fixed by means such as adhesion or welding while covering the widthwise ends of the top sheet 4. Thus, the top sheet 4 and the leak-proof sheet 5 wrap the absorbent core 3c to form the absorbent main body 3.

Rubber threads (not shown) may be provided, as elastic members, in both widthwise ends of the absorbent main body 3 along the longitudinal direction of the absorbent main body 3. Such rubber threads are for providing stretchability to parts of the absorbent main body 3 and parts of the exterior sheet 7 in the vicinity of the leg openings HL. The rubber threads are placed, for example, between the top sheet 4 and the leak-proof sheet 5, and are fixed to these sheets 4 and 5 with adhesive (e.g. hot-melt adhesive) while being extended by a predetermined ratio (two to four times of its original unstretched length).

In some cases, leakage-proof walls (not shown) for preventing side leakage of urine may be provided in the absorbent main body 3. Such leakage-proof walls are so-called barrier cuffs. The barrier cuffs are configured by flexible sheets such as nonwoven fabric, and are provided, for example, on both ends of the skin-side surface of the absorbent main body 3 so as to stand. However, the leakage-proof wall is well known, and the description thereof will be omitted.

The exterior sheet 7 is a flexible sheet having a substantially hourglass shape when viewed from above in the state in which a diaper 1 is spread out as shown FIG. 1B. The sheet 7 has three directions perpendicular to one another: the thickness direction; the longitudinal direction; and the width direction. The exterior sheet 7 is classified into three parts 7f, 7b and 7c in the longitudinal direction. That is, the exterior sheet 7 is classified into: a ventral part 7f arranged on the stomach side of a wearer; a dorsal part 7b arranged on the back side of a wearer; and a crotch part 7c arranged on the crotch of a wearer. It goes without saying that the crotch part 7c is located between the ventral part 7f and the dorsal part 7b. In a substantially hourglass shape when viewed from above, the crotch part 7c is a narrowed part 7c in the width direction.

As shown in FIG. 2, the exterior sheet 7 is made of a so-called laminated sheet 7 having a two-layer structure. That is, the exterior sheet 7 includes an inner-layer sheet 8 and an outer-layer sheet 9: the inner-layer sheet 8 faces the skin side of a wearer to serve as an inner layer; and the outer-layer sheet 9 faces the non-skin side of a wearer to serve as an outer layer. The inner-layer sheet 8 and the outer-layer sheet 9 are stacked in the thickness direction and are joined to each other by means such as adhesion or welding. In this example, welding is performed in a certain joining pattern (not shown) in which joined parts are discontinuously distributed.

The inner-layer sheet 8 is made of a stretchable sheet 8 having a stretchability in the width direction of a diaper 1. And, the outer-layer sheet 9 is made of a low-extensible sheet 9 having a low extensibility in the width direction of a diaper 1. The inner-layer sheet 8 having a stretchability is extended by a certain extension ratio corresponding to 2.5 times the original unstretched length in the width direction, for example (hereinafter referred to as an extended state), and the extended inner-layer sheet is stacked on the low extensible outer-layer sheet 9 which is stretched in the width direction. These sheets 8 and 9 are fixed to each other in the joining pattern in an integrated manner.

When the extended state is released, the inner-layer sheet 8 contracts in the width direction of the diaper 1 due to its stretchability. And, the outer-layer sheet 9 having a low extensibility bends in the width direction of the diaper 1 in the form of a plurality of creases. Thus, the outer-layer sheet 9 quickly follows the contraction of the inner-layer sheet 8, and the entire length of the outer-layer sheet 9 in the width direction decreases. Consequently, in a state in which external force is not exerted on a diaper 1, the entirety of the exterior sheet 7 shortens in the width direction, and simultaneously the outer surface of the exterior sheet 7 has a plurality of creases caused by the bending of the outer-layer sheet 9. However, pulling external force in the width direction is exerted on the exterior sheet 7, the exterior sheet 7 can extend almost elastically till the creases have completely stretched. That is, the exterior sheet 7 of a diaper 1 has a stretchability in the width direction.

The exterior sheet 7 in which the creases have completely stretched is in a maximum extended state, that is, a spread-out state shown in FIG. 1B. Hereinafter, concerning the exterior sheet 7 which is in the maximum extended state, the length of the exterior sheet 7 in the width direction of a diaper 1 is referred to as a "maximum extension length". The maximum extension length is different depending on the product size of a diaper. For example, the maximum extension length DLL for LL-size diapers is larger than the maximum extension length DL for L-size diapers; in this example, the maximum extension length DLL is 1.1 times as large as the maximum extension length DL. These maximum extension lengths DL and DLL are related to a feature of the invention to be described later.

The foregoing "stretchability" means a characteristic as follow: when pulling external force is exerted on an object, the object extends almost elastically in a direction in which the external force acts, and when the external force is released, the object contracts almost elastically. As mentioned above, a sheet having such a stretchability is the "stretchable sheet 8".

Further, it is preferable that the stretchable sheet 8 satisfies the following conditions. That is, concerning a band-like sheet having a lateral length of 25 mm, while the longitudinal ends of the band-like sheet being held equally throughout the entire lateral length of 25 mm, the band-like sheet is pulled in the longitudinal direction with an external force of 1.0(N) which is applied on the longitudinal ends, and. Under this condition, it is preferable that the elongation ratio (%) of the band-like sheet is any value from 50% to 300%. Simultaneously, it is preferable that a residual elongation (%) which is elongation remaining after a sheet has contracted by releasing the external force is any value from 0% to 40%. It is more preferable that the elongation ratio is any value from 70% to 200% and simultaneously the residual elongation is any value from 0% to 30%. Here, the elongation ratio (%) is the percentage of a value ($=\Delta L1/L0$) obtained by dividing a value $\Delta L1(=L1-L0)$ by an original unstretched length L0; the original unstretched length L0 is the length of a band-like sheet under no load which has not been pulled yet, and the value $\Delta L1(=L1-L0)$ is obtained by subtracting the original unstretched length L0 from the length L1 of a band-like sheet when the sheet is pulled with an external force of 1.0(N). The foregoing residual elongation (%) is the percentage of a value $(=\Delta L2/\Delta L1)$ obtained by dividing value $\Delta L2$ by the value $\Delta L1$; the value $\Delta L2$ $(=L2-L0)$ is obtained by subtracting the original unstretched length L0 (before the pulling) from the length L2 (after the external force of 1.0(N) is released), and the value $\Delta L1$ $(=L1-L0)$ is obtained by subtracting the original unstretched length L0 from the length L1 when the sheet is pulled with the foregoing external force.

The "low-extensible sheet 9" is a sheet having an extensibility lower than that of the stretchable sheet 8. That is, the "low-extensible sheet 9" is a sheet whose elongation ratio (%) when a pulling external force of a certain magnitude is exerted on the sheet is lower than the elongation ratio (%) of the stretchable sheet 8. It is preferable that such a low-extensible sheet 9 satisfies the following conditions. That is, concerning a band-like sheet having a lateral length of 25 mm, while the longitudinal ends of the band-like sheet being held equally throughout the entire lateral length of 25 mm, the band-like sheet is pulled in the longitudinal direction with an external force of 1.0(N) which is applied on the longitudinal ends. Under this condition, it is preferable that the elongation ratio (%) of the band-like sheet is any value from 0% to 20%. It is more preferable that the elongation ratio is any value from 0% to 10%.

The stretchable sheet 8 and low-extensible sheet 9 may be made of nonwoven fabric or woven fabric or film.

A nonwoven fabric which can be used as the stretchable sheet 8 is exemplified by nonwoven fabric which is produced by a suitable elongation (e.g. gear elongation) of a nonwoven fabric, the nonwoven fabric including thermoplastic elastomer fibers showing substantial elasticity and thermoplastic resin fibers showing substantial inelasticity. That is, as a result of the elongation, the thermoplastic resin fibers showing substantial inelasticity and being contained in the nonwoven fabric can be subject to plastic deformation. In addition, breaking joints of the fibers makes it possible to change the structure of the nonwoven fabric to a structure which is less likely to prevent the almost elastic stretching deformation of the thermoplastic elastomer fibers. Consequently, the stretchability of the nonwoven fabric is produced and the sheet can be used as a stretchable sheet 8.

As a thermoplastic elastomer showing substantial elasticity, there are polyurethane elastomer, polystyrene elastomer, polyolefin elastomer, polyamide elastomer, and the like. As a thermoplastic resin fibers showing substantial inelasticity, there is fiber containing polyolefin resin and the like. The polyolefin resin is exemplified by polyethylene (PE), polypropylene (PP), ethylene-α-olefin copolymer, and the like. In this example, the stretchable sheet 8 is a sheet made of nonwoven fabric produced by gear elongation, the combined nonwoven fabric containing polyurethane elastomer fiber and PP fiber.

A nonwoven fabric which can be used as the low-extensible sheet 9 is exemplified by spunbond nonwoven fabric, melted-blown nonwoven fabric, air-through nonwoven fabric, so-called SMS nonwoven fabric (laminating spunbond nonwoven fabric, melted-blown nonwoven fabric, and spunbond nonwoven fabric) and the like, which are composed of fiber made of PE, PP, polyester, polyamid. The configuration of fibers is not limited to the foregoing single fiber made of one thermoplastic resin. For example, composite fiber having a core-sheath structure of a PP core and a PE sheath may be employed, and other types of the foregoing fibers may also be employed. In this example, spunbond nonwoven fabric made of PP fiber is used as a low-extensible sheet 9.

As shown in FIGS. 1B and 2, the foregoing absorbent main body 3 is attached to the skin-side surface of the exterior sheet 7 having the foregoing two-layer structure, that is, the body 3 is attached to the widthwise center on the skin-side surface of the inner-layer sheet 8. And the absorbent main body 3 is attached to the exterior sheet 7 so that the longitudinal direction of the absorbent main body 3 is aligned to the longitudinal direction of the exterior sheet 7. The attaching is made by joining at least the longitudinal ends 3e and 3e of the absorbent main body 3 to the exterior sheet 7. In this example, as shown in FIG. 2, on the longitudinal ends 3e and 3e, substantially T-shaped joined parts j and j are formed which join the absorbent main body 3 and the exterior sheet 7. That is, each of the joined parts j and j includes: a widthwise band-like part jW and a longitudinal band-like part jL. The widthwise band-like part jW is elongated in the width direction of the diaper 1, and the longitudinal band-like part jL extends toward the crotch part 7c from the widthwise central part of the widthwise band-like part jW. This makes it possible to effectively prevent the absorbent main body 3 and the exterior sheet 7 from unnecessarily constraining each other. However, the shape of the joined parts j is not limited thereto. For example, a spot of an additional joined part jC may be provided at a position between a pair of T-shaped joined parts j and j. Or, on each of the longitudinal ends 3e and 3e of the absorbent main body 3, a substantially rectangular joined part (not shown) having substantially the same area as the longitudinal end 3e may be formed. Or, a joined part having any other shape may be formed. In this example, forming of the joined parts j is achieved by adhesion with hot-melt adhesive. However, the invention is not limited thereto. For example, welding may be applied.

In this example, when attaching the absorbent main body 3 to the exterior sheet 7, the exterior sheet 7 is in a widthwise extended state in which the exterior sheet 7 is loosed compared to the inner-layer sheet 8 which is in an extended state at the time of fixing the outer-layer sheet 9 to the inner-layer sheet 8 (corresponding to a "reference extended state" and a "maximum extended state" to be described later). The foregoing extended state in which the exterior sheet 7 is loosed is referred to as a "the pitch-P0 extended state", and will be described later. Accordingly, when a pull-on diaper 1 is finally finished, the absorbent main body 3 is less likely to crease. This makes it possible to effectively prevent troubles such as urine leakage and liquid-absorbency deterioration of the absorbent main body 3. In the below description of the manufacturing line LM, there is described that attaching of the absorbent main body 3 to the exterior sheet 7 is made in the extended state in which the sheet 7 is loosed.

The exterior sheet 7 to which the absorbent main body 3 is attached as shown in FIG. 1B is two-folded on its crotch part 7c. And, its ventral part 7f and its dorsal part 7b are stacked. The ventral part 7f and the dorsal part 7b which are stacked are joined on the widthwise ends 7eW, to be in a form of a pull-on diaper 1, in which a waist opening HB and a pair of leg openings HL and HL are formed as shown in FIG. 1A.

Figure 3A:
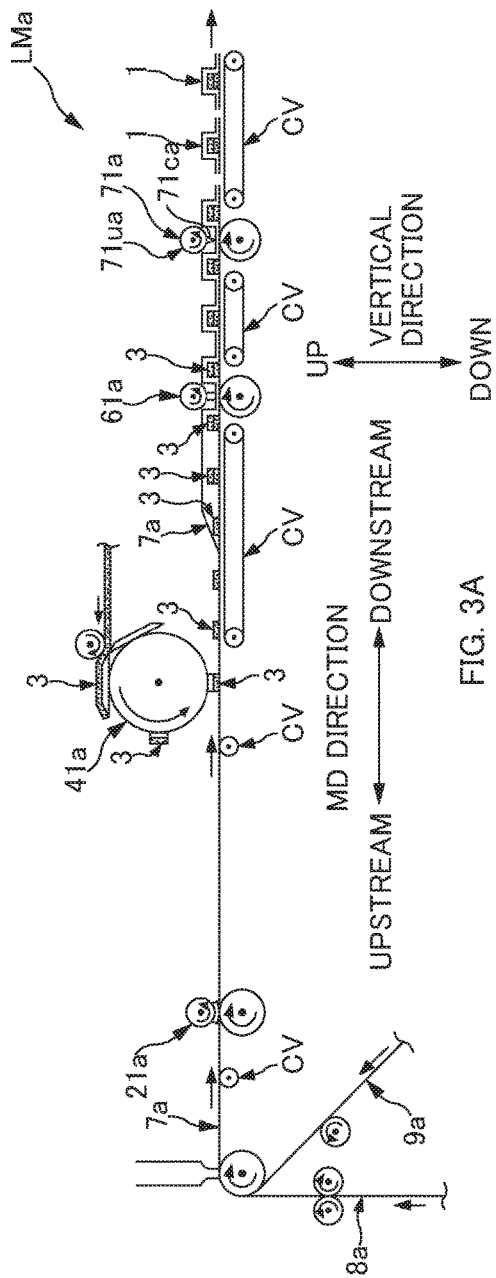
FIG. 3A is a schematic side view of a manufacturing line LMa of a diaper 1 according to reference example.
Figure 3B:
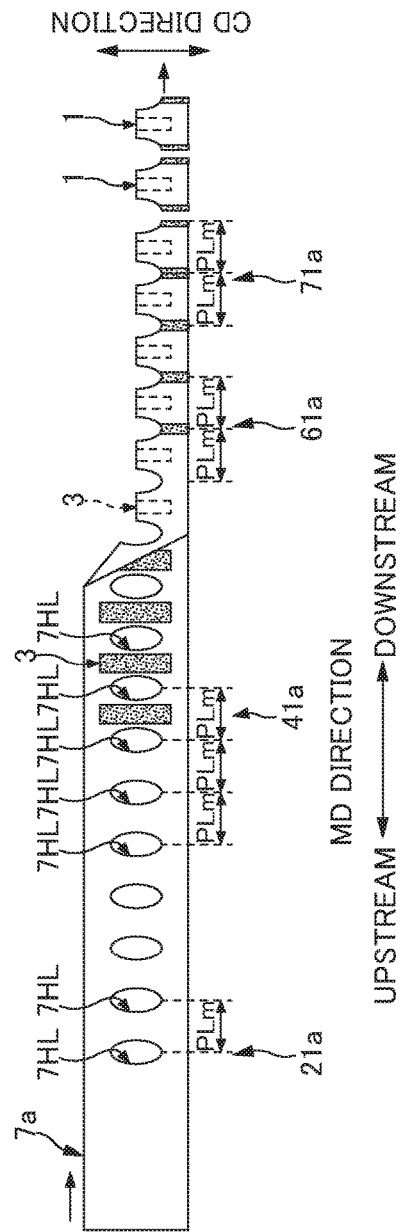
FIG. 3B is a schematic plan view showing how diapers 1 are manufactured.

Such a diaper 1 is manufactured in a manufacturing line LMa of the diaper. FIG. 3A is a schematic side view of a manufacturing line LMa according to a reference example, and FIG. 3B is a plan view showing how diapers 1 are manufactured in FIG. 3A.

First in this manufacturing line LMa of the reference example, the substrate sheet 7a of diapers 1 is produced. The substrate sheet 7a is continuously transported along a predetermined transporting direction by means such as suitable transport mechanisms CV, CV . . . . During the transportation, the substrate sheet 7a is subject to various processes such as attaching components or die-cutting. After every process, the substrate sheet 7a is sequentially processed, and a diaper 1 shown in FIG. 1A is finally manufactured. In this example, as shown in FIG. 3B, the substrate sheet 7a is transported basically in a so-called lateral-direction flowing. That is, the substrate sheet 7a is transported in a state in which a direction corresponding to the width direction of the diapers 1 is aligned to the transporting direction and a state in which pieces to be diapers 1 are lined up in the transporting direction. In the reference example, the substrate sheet 7a is transported in the transverse direction flowing as mentioned above, and the same is applied to the manufacturing line LM (to be described later, FIGS. 4A and 4B) according to the present embodiment.

In the manufacturing line LMa of the reference example, the continuous sheet 7a of the exterior sheet 7 (hereinafter merely referred to as an exterior sheet 7a) is used as the substrate sheet 7a. For the purpose of stability of the transportation, the exterior sheet 7a remains in the maximum extended state throughout substantially the entire length of the manufacturing line LMa in the transporting direction. The maximum extended state means a state in which the creases of the outer-layer sheet 9(9a) (the low-extensible sheet of the exterior sheet 7(7a) having two-layer structure) have completely stretched, as mentioned above. In the exterior sheet 7a in the maximum extended state, parts to be a diaper 1 are lined up in the transporting direction at a pitch PLm which is equal to the maximum extension length DL of the foregoing diaper 1.

In the case of the reference example, the processing apparatuses 21a, 41a, 61a and 71a in the manufacturing line LMa can perform processes to the exterior sheet 7a for each part to be a diaper 1, because the processes are performed to the exterior sheet 7a at the pitch PLm which is equal to the maximum extension length DL. For example, the rotary cutter device 71a, which is an example of the processing apparatus, includes cutter blades 71ca on the outer circumferential surface of its roll 71ua. The cutter blades 71ca serve as a processing portion, and are located at an arrangement pitch in the rotating direction equal to the maximum extension length DL. Accordingly, the roll 71ua synchronizes and rotates with no sliding relative to the exterior sheet 7a, and the process for each part to be a diaper 1 is realized.

However, if a plurality types of diapers 1 having different product sizes (e.g. L-size diapers and LL-size diapers) are manufactured in the manufacturing line LMa, a maximum extension length DL for L-size diapers, and a maximum extension length DLL for LL-size diapers are different from each other. Accordingly, in the example of the cutter apparatus 71, the cutter roll 71ua for LL-size diapers is needed in addition to the cutter roll 71ua for L-size diapers. That is, a plurality of rolls corresponding to the product sizes are needed. This may cause a problem such as facilities-cost increase.

FIG. 4A is a schematic side view of a manufacturing line LM according to the present embodiment, which can solve the foregoing problem. FIG. 4B is a plan view showing how diapers 1 are manufactured in FIG. 4A.

In this manufacturing line LM, the processing devices 41, 61 and 71 can be shared regardless of the product size of a diaper 1 to be manufactured. The detail is as follow.

The manufacturing line LM includes: upstream transport mechanisms CVu, CVu . . . which transports the exterior sheet 7a in the transporting direction; and downstream transport mechanisms CVd, CVd . . . which are located downstream in the transporting direction from the upstream transport mechanisms CVu, CVu . . . . Between the upstream transport mechanisms CVu, CVu . . . and the downstream transport mechanisms CVd, CVd . . . , an extension-ratio adjustment unit (corresponding to the extension-ratio adjustment mechanism) is arranged which adjusts the extension ratio at which the exterior sheet 7a extends in the transporting direction. And, each of the processing devices 41, 61 and 71 is arranged at a position for each downstream transport mechanism CVd. Accordingly, the processing devices 41, 61 and 71 perform their own processes to the exterior sheet 7a which is being transported by their corresponding downstream transport mechanisms CVd, CVd . . . .

In the manufacturing line LM, an exterior sheet 7a for L-size diapers (corresponding to the first stretchable sheet-like member) and an exterior sheet 7a for LL-size diapers (corresponding to the second stretchable sheet-like member) are processed as follow.

In the case of manufacturing L-size diaper 1, the exterior sheet 7a for L-size diapers is supplied to the upstream transport mechanisms CVu, CVu . . . from upstream. For the purpose of stability of the transportation, the mechanisms CVu, CVu . . . transport the exterior sheet 7a being in the maximum extended state. That is, the exterior sheet 7a for L-size diapers is transported being in a state in which parts to be a diaper 1 are lined up in the transporting direction at the pitch PLm (corresponding to the first pitch) which is equal to the maximum extension length DL for L-size diapers 1.

But, in the extension-ratio adjustment unit 30 located downstream, the extension ratio of the exterior sheet 7a is reduced in order to suppress creases of the foregoing absorbent main body 3. And, the extension ratio is adjusted so that parts to be a diaper 1 are lined up at a predetermined pitch P0 which is smaller than the pitch PLm. And, the exterior sheet 7a is transferred to the downstream transport mechanisms CVd, CVd . . . . The downstream transport mechanisms CVd, CVd . . . transport the exterior sheet 7a for L-size diapers as it is while the predetermined pitch P0 remaining. Accordingly, the processing devices 41, 61 and 71 perform their own processes to the exterior sheet 7a at the predetermined pitch P0. Thus, the exterior sheet 7a undergoes the processes quickly for each part to be a diaper 1.

On the other hand, in the case of manufacturing LL-size diaper 1, the exterior sheet 7a for LL-size diapers is supplied to the upstream transport mechanisms CVu, CVu . . . from upstream. Also, concerning the exterior sheet 7a for LL-size diapers, for the purpose of stability of the transportation, the mechanisms CVu, CVu . . . transport the exterior sheet 7a being in the maximum extended state. That is, the exterior sheet 7a for LL-size diapers is transported being in a state in which parts to be a diaper 1 are lined up in the transporting direction at the pitch PLLm (corresponding to the second pitch) which is equal to the maximum extension length DLL for LL-size diapers 1. In the extension-ratio adjustment unit 30 located downstream, like the foregoing exterior sheet 7a for L-size diapers, the extension ratio of the exterior sheet 7a for LL-size diapers is reduced in order to suppress creases of the absorbent main body 3.

But, as mentioned above, the maximum extension length DLL is 1.1 times as large as the maximum extension length DL for L-size diapers, and in other words, is different from the maximum extension length DL for L-size diapers. And, in the extension-ratio adjustment unit 30, the extension ratio is adjusted by an adjustment amount corresponding to the maximum extension length DLL of the exterior sheet 7 for LL-size diapers. Accordingly, as is the case of the exterior sheet 7*a* for L-size diapers, parts to be a diaper 1 in the exterior sheet 7*a* for LL-size diapers are lined up at the predetermined pitch P0. The downstream transport mechanisms CVd, CVd . . . transport the exterior sheet 7*a* as it is while the predetermined pitch P0 remaining. In other words, as is the case of the exterior sheet 7*a* for L-size diapers, the exterior sheet 7*a* for LL-size diapers is transported being in a state in which parts to be a diaper 1 are lined up at the predetermined pitch P0. Accordingly, if the processing devices 41, 61 and 71 perform their own processes at the foregoing predetermined pitch P0, the exterior sheet 7*a* for LL-size diapers can undergo the processes for each part to be a diaper 1. That is, the processing devices 41, 61 and 71 can be shared for L-size diapers and LL-size diapers.

In the manufacturing line LM, a plurality of processing units 10, 20 . . . (including the processing units 40, 60, 70 in which the foregoing processing devices 41, 61 and 71 are included) are arranged being lined up in the transporting direction. In this example, as the plurality of processing units 10, 20 . . . , there are included an exterior-sheet producing unit 10, a leg-opening forming unit 20, the extension-ratio adjustment unit 30, an absorbent-main-body attaching unit 40, a two-folded unit 50, an end-section sealing unit 60 and a dividing unit 70.

As can be seen in the above description, transportation in the area upstream in the transporting direction from the extension-ratio adjustment unit 30 is performed by the foregoing upstream transport mechanisms CVu, CVu . . . , and transportation in the area downstream from the extension-ratio adjustment unit 30 is performed by the foregoing downstream transport mechanisms CVd, CVd . . . . Known transport mechanisms are used as the upstream transport mechanisms CVu and the downstream transport mechanisms CVd. There are, for example, transport rollers, suction belt conveyors whose belt surfaces (serving as placement faces) have suction-holding function, or belt conveyors having pairs of upper and lower endless belts between which the transport path of the exterior sheet 7*a* is placed.

In the description below, the transporting direction defined on the manufacturing line LM is referred to as "MD direction". One of two directions perpendicular to MD direction is referred to as "CD direction", and the other direction is referred to as "Z direction". CD direction is parallel to the width direction of the exterior sheet 7*a*, and is in a direction perpendicular to the paper plane in FIG. 4A. Z direction is parallel to the thickness direction of the exterior sheet 7*a*.

The exterior-sheet producing unit 10, which is the first processing unit, produces the exterior sheet 7*a* for L-size diapers and the exterior sheet 7*a* for LL-size diapers. The exterior sheet 7*a* is the substrate sheet 7*a* of the diapers 1, and continues in MD direction. That is, a stretchable sheet 8 (serving as the inner-layer sheet 8) is transported along MD direction, and a continuous sheet 8*a* of the stretchable sheet 8, which was in substantially an original unstretched length, extends in MD direction by a certain extension ratio (the continuous sheet 8*a* is hereinafter merely referred to as a "stretchable sheet 8*a*"). Simultaneously, the stretchable sheet 8*a* in the extended state is stacked on and joined to a continuous sheet 9*a* of low-extensible sheet 9 from the thickness direction, the continuous sheet 9*a* (the outer-layer sheet 9) being extended and tightened (the continuous sheet 9*a* is hereinafter merely referred to as a "low-extensible sheet 9*a*"). Consequently, the exterior sheet 7*a* is produced as the substrate sheet 7*a*.

For the purpose of producing the exterior sheet 7*a*, the exterior-sheet producing unit 10 includes: a transport mechanism 11 for the stretchable sheet 8*a*; a transport mechanism 13 for the low-extensible sheet 9*a*; and an ultrasonic welding device 15.

The main body of the transport mechanism 11 for the stretchable sheet 8*a* is, for example, a nip-roll mechanism. That is, the mechanism 11 includes a pair of nip rolls 11R and 11R which rotate respectively about rotational axes along CD direction. The pair of nip rolls 11R and 11R are driven and rotated by obtaining driving force from a servo motor (serving as a power source, not shown) while the stretchable sheet 8*a* for L-size diapers or for LL-size diapers, which is continuously transported from the upstream process, is being sandwiched between the outer circumferential surfaces of the nip rolls 11R and 11R. Thereby, the stretchable sheet 8*a* is transferred to the ultrasonic welding device 15.

On the other hand, the main body of the transport mechanism 13 for the low-extensible sheet 9*a* is, for example, a transport roller 13R which rotates about a rotational axis along CD direction. The transport roller 13R is driven and rotated by obtaining driving force from a servo motor (serving as a power source, not shown) while the outer circumferential surface of the roller 13R being in contact with the low-extensible sheet 9*a* for L-size diapers or for LL-size diapers, which is continuously transported from the upstream process. Thereby, the low-extensible sheet 9*a* is transferred to the ultrasonic welding device 15.

The ultrasonic welding device 15 includes: a horn 15*h* having a vibrating surface which vibrates ultrasonically; and an anvil roller 15*a* whose outer circumferential surface receives ultrasonic vibration of the vibrating surface of the horn 15*h*. The anvil roller 15*a* is supported being capable of rotating about a rotational axis along CD direction, and is driven and rotated by obtaining driving force from a servo motor (serving as a power source, not shown). The stretchable sheet 8*a* and the low-extensible sheet 9*a*, which have been transferred from the transport mechanisms 11 and 13, are wound around the outer circumferential surface of the anvil roller 15*a* at a certain wrapping angle (45° degrees or more) with substantially no sliding relative to the outer circumferential surfaces.

Accordingly, the anvil roller 15*a* is driven and rotated, and thereby the stretchable sheet 8*a* and the low-extensible sheet 9*a* are both transported, along the outer circumferential surface of the anvil roller 15*a*, at a conveying speed which is substantially same as the circumferential speed value V15*a* of the anvil roller 15*a*. The stretchable sheet 8*a* and the low-extensible sheet 9*a* pass the position of the horn 15*h* while the stretchable sheet 8*a* and the low-extensible sheet 9*a* being stacked in the thickness direction on the outer circumferential surface of the anvil roller 15*a*. At this stage, ultrasonic vibration energy is applied to these sheets 8*a* and 9*a* from the vibrating surface of the horn 15*h*, and these sheets 8*a* and 9*a* generate heat and melt. Thus, the sheets 8*a* and 9*a* are joined to each other in a joining pattern in which a plurality of the joined parts are discontinuously distributed. And, the exterior sheet 7*a* is consequently produced. The anvil roller 15*a* sends the exterior sheet 7*a* toward downstream in MD direction, and then the exterior sheet 7*a* is transported to the leg-opening forming unit 20 located downstream in MD direction, at a conveying speed which is substantially same as the circumferential speed value V15*a*.

Here, concerning the transport mechanism 11 of the stretchable sheet 8a, the circumferential speed value V11R (m/min.) of the nip roll 11R is substantially same as the conveying speed (m/min.) of the stretchable sheet 8a which is transported from the upstream process, the stretchable sheet 8a for L-size diapers or for LL-size diapers being in substantially the original unstretched length. On the other hand, the circumferential speed value V15a (m/min.) of the anvil roller 15a, being located downstream thereof, is set to a value of the circumferential speed value V11R (m/min.) of the nip roll 11R multiplied by the extension ratio. Accordingly, when the stretchable sheet 8a passes between the nip-roll mechanism 11 and the anvil roller 15a, the stretchable sheet 8a extends from the original unstretched length till the length corresponding to the extension ratio. The stretchable sheet 8a passes the position of the horn 15h in the extended state. On the other hand, concerning the transport mechanism 13 of the low-extensible sheet 9a, the circumferential speed value V13R (m/min.) of the transport roller 13R is substantially same as the conveying speed (m/min.) of the low-extensible sheet 9a for L-size diapers or for LL-size diapers which is transported from the upstream process. The conveying speed (m/min.) is also substantially same as the circumferential speed value V15a (m/min.) of the anvil roller 15a. Accordingly, the low-extensible sheet 9a remains in a state in which the sheet 9a is properly extended and tightened to substantially an extent that does not undergo plastic deformation or the like. On the anvil roller 15a, the low-extensible sheet 9a which has been extended and tightened is stacked on and joined to the stretchable sheet 8a which has extended till the length corresponding to the extension ratio.

The low-extensible sheet 9a which is extended and tightened is in a so-called fully-extended state in which a sheet having a low extensibility is difficult to further extend. Accordingly, even if an unexpectedly great tension is exerted during subsequent transportation, the low-extensible sheet 9a can resist the tension so that the length of the exterior sheet 7a in MD direction does not change. Accordingly, the subsequent forming of the leg opening 7HL in the exterior sheet 7a can be made with high positioning accuracy. The foregoing "fully-extended state" can be defined as, for example, "a state in which a sheet is not damaged and cannot further extend at the elongation ratio of 5% or more from the current no-loop state".

The foregoing "extension ratio" indicates how many times as long as the original unstretched lengths of the stretchable sheet 8a the entire length of the sheet 8a in an extended state is. And, the "extension ratio" defines how much the exterior sheet 7 (7a) of a finished diaper 1 can extend in the width direction of the diaper 1 from a state in which no force is exerted on the sheet 7 (7a). That is, in a diaper 1 which has been manufactured when the setting of the stretchable sheet 8a is in a certain extension ratio, the exterior sheet 7 (7a) can extend in the width direction of a diaper 1 till the extended state, corresponding to the foregoing extension ratio. The extension ratio is set, for example, to any value from 1.5 times to 4 times.

In both cases of producing the exterior sheet 7a for L-size diapers and producing the exterior sheet 7a for LL-size diapers, the extension ratios is set to any value within the foregoing range. In the description below, the extension ratio of the exterior sheet 7a for L-size diapers is set to ML times the original unstretched length, and the extension ratio of for LL-size diapers exterior sheet 7a is set to MLL times the original unstretched length. In the description below, a state in which the stretchable sheet 8a extends by the exterior-sheet producing unit 10 till the predetermined extension ratio is also referred to as a "reference extended state".

In the leg-opening forming unit 20 in the next process, the extended state of the exterior sheet 7a remains in the reference extended state mentioned above. That is, in the case of L-size diaper, the exterior sheet 7a is transported in an extended state in which the exterior sheet 7a extends at an extension ratio of the foregoing ML times, and in the case of LL-size diaper, the exterior sheet 7a is transported in an extended state in which the exterior sheet 7a extends at an extension ratio of the foregoing MLL times. These extended states correspond to the foregoing maximum extended state. In the leg-opening forming unit 20, the exterior sheet 7a in the maximum extended state is being transported. And, the leg opening 7HL for a L-size diaper is formed by die-cutting the exterior sheet 7a at the pitch PLm, and the leg opening 7HL for LL-size is formed by die-cutting the exterior sheet 7a at the pitch PLLm.

Here, such pitches PLm and PLLm respectively correspond to the lengths in MD direction of a single diaper in their own maximum extended states. In other words, the pitches PLm and PLLm are respectively equal to the foregoing maximum extension lengths DL and DLL. Accordingly, in this example, the pitch PLLm for LL-size diapers is 1.1 times as large as the pitch PLm for L-size diapers. Since the pitches PLm and PLLm are pitches in their own maximum extended states, the pitches PLm and PLLm are respectively maximum pitches of the exterior sheet 7a for L-size diapers and of the exterior sheet 7a for LL-size diapers. Hereinafter, the pitch PLm and the pitch PLLm in their own maximum extended states are referred to as a "maximum pitch PLm" and a "maximum pitch PLLm".

The forming the leg opening 7HL is performed by a so-called die cutter device 21. But, the pitch PLm for L-size diapers and the pitch PLLm for LL-size diapers are different as mentioned above. Accordingly, the leg-opening forming unit 20 includes a die cutter device 21 for L-size diapers and a die cutter device for LL-size diapers. Every time when changing the product size, the die cutter device 21 is replaced with one for corresponding size.

The main structure difference between these die cutter devices 21 and 21 is their sizes, and other configurations are substantially the same. That is, both die cutter devices 21 and 21 includes a pair of upper and lower rolls 21u and 21d which rotate respectively about rotational axes along CD direction while their outer circumferential surfaces facing each other. The upper roll 21u is a cutter roll 21u having a cutter blade 21c on the outer circumferential surface. And, the lower roll 21d is an anvil roll 21d which receives the cutter blade 21c on its smooth outer circumferential surface. The cutter blade 21c is a so-called annular cutting die whose shape corresponds to the shape of the leg opening 7HL. The cutter blade 21c is provided protruding from the outer circumferential surface 21us of the cutter roll 21u. Accordingly, when the exterior sheet 7a passes the nip between the upper and lower rolls 21u and 21d, the section of the exterior sheet 7a which is located inside the annular cutter blade 21c is cut out from the exterior sheet 7a by die-cutting. Consequently, a leg opening 7HL is formed in the exterior sheet 7a.

In this example, the power source by which the upper and lower rolls 21u and 21d are driven and rotated is a servo motor (not shown). The upper roll 21u includes a single cutter blade 21c on its outer circumferential surface. Accordingly, every time when the exterior sheet 7a for L-size diapers passes the die cutter device 21 by the length of the pitch PLm in MD direction, the upper and lower rolls 21u and 21*d* for L-size diapers rotate once and the leg openings 7HL are thereby formed at the pitch PLm in MD direction in the exterior sheet 7*a* for L-size diapers. Similarly, every time when the exterior sheet 7*a* for LL-size diapers passes the die cutter device 21 by the length of the pitch PLLm in MD direction, the upper and lower rolls 21*u* and 21*d* for LL-size diapers rotate once, and the leg openings 7HL are thereby formed at the pitch PLLm in the exterior sheet 7*a* for LL-size diapers.

Concerning the die cutter device 21 for L-size diapers, in order to perform die-cutting with substantially no sliding relative to the exterior sheet 7*a*, the rotation radius at the position of the cutting edge of the cutter blade 21*c* of upper roll 21*u* is defined based on the pitch PLm at which the leg openings 7HL are to be formed. Similarly, the rotation radius of the outer circumferential surface of the lower roll 21*d* is defined based on the pitch PLm. That is, concerning the die cutter device 21 for L-size diapers, the rotation radius at the position of the cutting edge of the upper roll 21*u* and the rotation radius of the outer circumferential surface of the lower roll 21*d* are set to a value obtained by dividing the pitch PLm by 2*n* (two times pi). This enables the die cutter device 21 for L-size diapers to form the leg openings 7HL precisely at the pitch PLm, in the exterior sheet 7*a* which is in the maximum extended state. Then, the exterior sheet 7*a* which is in the maximum extended state is transferred to the extension-ratio adjustment unit 30 downstream in MD direction. The same is also true for the die cutter device 21 for LL-size diapers. That is, concerning the die cutter device 21 for LL-size diapers, the rotation radius at the position of the cutting edge of the upper roll 21*u* and the rotation radius of the outer circumferential surface of the lower roll 21*d* are set to a value obtained by dividing the pitch PLLm by 2*n* (two times pi). Similar to the case in L-size diapers, this effectively prevents sliding relative to the exterior sheet 7*a*.

In the extension-ratio adjustment unit 30 in the next process, the exterior sheet 7*a* which is being transported in the maximum extended state contracts in MD direction. Consequently, the exterior sheet 7*a* becomes in an extended state in which the extension ratio is smaller than the extension ratios ML and MLL in the maximum extended state. This prevents possible creasing of the absorbent main body 3, which will be subsequently attached to the exterior sheet 7*a*.

In the contraction process, both of the exterior sheet 7*a* for L-size diapers and the exterior sheet 7*a* for LL-size diapers are adjusted so that the pitch PL and the pitch PLL at which parts to be a diaper 1 are lined up are identical to the predetermined pitch P0. In other words, in the contraction process, the exterior sheet 7*a* for LL-size diapers contracts more than the exterior sheet 7*a* for L-size diapers contracts. For example, since, in the maximum extended state, the pitch PLLm for LL-size diapers is 1.1 times as much as the pitch PLm for L-size diapers, the exterior sheet 7*a* for LL-size diapers contracts more than the exterior sheet 7*a* for L-size diapers by 0.1 times. Accordingly, after the contraction, the pitch PL in the exterior sheet 7*a* for L-size diapers and the pitch PLL in the exterior sheet for LL-size diapers are equal to the predetermined pitch P0.

Through the subsequent transportation, the state in which parts to be a diaper 1 are lined up at the predetermined pitch P0 is maintained. Accordingly, the processing devices 41, 61 and 71 of the subsequent processing units 40, 60 and 70 can be shared by both of the exterior sheet 7*a* for L-size diapers and the exterior sheet 7*a* for LL-size diapers. Hereinafter, an extended state in which parts to be a diaper 1 are lined up at the predetermined pitch P0 is also referred to as a "pitch-P0 extended state".

As mentioned above, the degree of contraction of the exterior sheet 7*a* are different depending on the product size. Here, a shrinkage ratio Rr is defined as a value indicating the degree of contraction as follow. In the case of L-size diapers, the shrinkage ratio Rr is a value (=(PLm−P0)/PLm) obtained by dividing a value (PLm−P0) by the pitch PLm; the value (PLm−P0) is obtained by subtracting the predetermined pitch P0 from the pitch PLm in the maximum extended state. In the case of LL-size diapers, the shrinkage ratio Rr (<1) is a value (=(PLLm−P0)/PLLm) obtained by dividing a value (PLLm−P0) by the pitch PLLm; the value (PLLm−P0) is obtained by subtracting the predetermined pitch P0 from the pitch PLLm in the maximum extended state. As is apparent from the foregoing description, the shrinkage ratio Rr for LL-size diapers is larger than the shrinkage ratio Rr for L-size diapers, by 0.1 times the extension ratio.

On the other hand, the contraction of the exterior sheet 7*a* according to the shrinkage ratio Rr is performed by two nip-roll mechanisms 31 and 33 provided being lined up in MD direction. The detail is as follow.

The upstream nip-roll mechanism 31 is arranged at a predetermined position in MD direction, and the downstream nip-roll mechanism 33 is arranged at a position downstream from the upstream nip-roll mechanism 31. These nip-roll mechanisms 31 and 33 have substantially the same configuration. That is, the upstream nip-roll mechanism 31 includes a pair of upper and lower nip rolls 31*u* and 31*d* which rotate respectively about rotational axes along CD direction. Also, the downstream nip-roll mechanism 33 includes a pair of upper and lower nip rolls 33*u* and 33*d* which rotate respectively about rotational axes along CD direction. The pair of nip rolls 31*u* and 31*d* of the upstream nip-roll mechanism 31 are driven and rotated by obtaining driving force from a servo motor (serving as a power source, not shown) while the exterior sheet 7*a* is being sandwiched between the outer circumferential surfaces of the nip rolls 31*u* and 31*d*. Thereby, the exterior sheet 7*a* is transferred downstream in MD direction. Similarly, the pair of nip rolls 33*u* and 33*d* of the downstream nip-roll mechanism 33 are driven and rotated by obtaining driving force from a servo motor (serving as a power source, not shown) while the exterior sheet 7*a* is being sandwiched between the outer circumferential surfaces of the nip rolls 33*u* and 33*d*. Thereby, the exterior sheet 7*a* is transferred further downstream in MD direction.

Here, the circumferential speed value V31 (m/min.) of the nip rolls 31*u* and 31*d* of the upstream nip-roll mechanism 31 is substantially same as the circumferential speed value V15*a* (m/min.) of the anvil roller 15*a* of the foregoing ultrasonic welding device 15. Accordingly, the circumferential speed value V31 of the nip rolls 31*u* and 31*d* is substantially same as the conveying speed (m/min.) of the exterior sheet 7*a* for L-size or LL-size diapers, which is being transported in the maximum extended state at a position immediately upstream from the nip rolls 31*u* and 31*d*. On the other hand, the circumferential speed value V33 (m/min.) of the nip rolls 33*u* and 33*d* of the downstream nip-roll mechanism 33 is smaller by the shrinkage ratio Rr than the circumferential speed value V31 of the nip rolls 31*u* and 31*d* of the upstream nip-roll mechanism 31. In other words, the circumferential speed value V33 is a multiplied value (=(1−Rr)×V31) obtained by multiplying the circumferential speed value V31 by a subtraction value (1−Rr), the subtraction value being obtained by subtracting the shrinkage ratio Rr from 1. Accordingly, while the exterior sheet 7a is passing the transport path R30 between the upstream nip-roll mechanism 31 and the downstream nip-roll mechanism 33, the exterior sheet 7a contracts to be in the second extended state; the extension ratio in the second extended state being smaller by 10% than the extension ratio in the first extended state. The exterior sheet 7a in the second extended state is transported to the absorbent-main-body attaching unit 40 located downstream in MD direction.

In the absorbent-main-body attaching unit 40 in the next process, the exterior sheet 7a is being transported in the second extended state, and the absorbent main body 3 is attached to the exterior sheet 7a at the predetermined pitch P0 in MD direction. On the other hand, in both cases of the exterior sheet 7a for L-size diapers and the exterior sheet 7a for LL-size diapers, the exterior sheet 7a remains in the pitch-P0 extended state when the exterior sheet 7a passes the processing unit 40. In the exterior sheet 7a in the pitch-P0 extended state, parts to be a diaper 1 are lined up at the predetermined pitch P0. Accordingly, in both cases of the exterior sheet 7a for L-size diapers and the exterior sheet 7a for LL-size diapers, a single rotating-drum device 41 (corresponding to the processing apparatus) included in the processing unit 40 can attach an absorbent main body 3 for each part to be a diaper 1. That is, it is possible to share the rotating-drum device 41 in both cases of L-size diapers and LL-size diapers.

The rotating-drum device 41 includes: a rotating drum 42 which rotates about a rotational axis along CD direction; a servo motor (not shown) which serves as a power source and which drives and rotates the rotating drum 42; and a plurality of holding pads 43, 43 . . . provided along the rotating direction on the outer circumferential surface of the rotating drum 42. Each holding pad 43 has a holding plane which is capable of sucking and holding the absorbent main body 3, and the holding plane faces outside in the rotation radius of the rotating drum 42. By the rotation of the holding pad 43 about the axis which is located at the plane center of its holding plane, the longitudinal direction of an absorbent main body 3 held by the holding plane changes from MD direction to CD direction.

Each holding pad 43 is configured so as to reciprocate relative to the rotating drum 42 within a certain range in the rotating direction. Such a reciprocating motion is produced by a suitable cam mechanism (not shown) from a rotation of the rotating drum 42. Accordingly, a pitch in the rotating direction between adjacent holding pads 43 and 43 can be changed depending on the position of the rotating drum 42 in the rotating direction. That is, at a first position S1 in the rotating direction, a space between adjacent holding pads 43 and 43 can be narrow, and at a second position S2 in the rotating direction, a space between adjacent holding pads 43 and 43 can be wide.

Here, at the first position S1, a plurality of the absorbent main bodies 3 are supplied in the form of continuous body 3a which continues in MD direction. When each holding pad 43 passes the first position S1, the pad 43 sucks and receives the continuous body 3a of the absorbent main body. And then, the cutter apparatus 45 located near the pad 43 divides the continuous body 3a, and a single sheet of the absorbent main body 3 is produced on the holding pad 43. The holding pad 43, as it is, moves to the second position S2 in the rotating direction by rotation of the rotating drum 42. During the movement, the holding pad 43 rotates as mentioned above, and the longitudinal direction of the absorbent main body 3 is thereby changed from MD direction to CD direction. In addition thereto, the holding pad 43 reciprocates during the movement, and a pitch between adjacent holding pads 43 and 43 is thereby changed to the predetermined pitch P0. Further, at the second position S2, the transport path of the exterior sheet 7a is placed closely to the unit 40. Accordingly, the rotating-drum device 41 can attach the absorbent main bodies 3, at the predetermined pitch P0 in MD direction, to the exterior sheet 7a which is in the pitch-P0 extended state.

The absorbent main body 3 is attached to a position between the leg openings 7HL and 7HL which are adjacent in MD direction in the exterior sheet 7a. In this example, in the foregoing extension-ratio adjustment unit 30, the transportation state of the exterior sheet 7a is adjusted so that the absorbent main body 3 is attached to the predetermined target position in the exterior sheet 7a. The adjustment is performed by an adjustment device 35, and the adjustment device 35 will be described later.

In the two-folding unit 50 in the next process, the exterior sheet 7a for L-size or LL-size diapers onto which the absorbent main bodies 3 are attached is two-folded in CD direction at a folding position, which is substantially a central part of the exterior sheet 7a in CD direction corresponding to the crotch part 7c of a diaper 1. Thus, in the exterior sheet 7a, one end section of the sheet 7a in CD direction is stacked on the other end section in the thickness direction. One end section finally becomes the ventral part 7f of a diaper 1, and other end section finally becomes the dorsal part 7b of the diaper 1.

The two-folding of the exterior sheet 7a is performed by a two-fold guiding member (not shown) arranged at a predetermined position in MD direction. The two-fold guiding member is a known configuration, and is composed of a combination of a plurality of suitable bars, for example. When the exterior sheet 7a passes the position of the two-fold guiding member, the guiding member folds gradually the exterior sheet 7a at the folding position, which is substantially a central part of the exterior sheet 7a in CD direction. When the exterior sheet 7a has completely passed the two-fold guiding member, the exterior sheet 7a is two-folded.

In the two-folding unit 50, the extended state of the exterior sheet 7a remains the pitch-P0 extended state mentioned above. While the exterior sheet 7a remaining in this extended state, the exterior sheet 7a is transferred downstream in MD direction.

In the next end-section sealing unit 60, the exterior sheet 7a for L-size or LL-size diapers remains in the pitch-P0 extended state. In the end-section sealing unit 60, the exterior sheet 7a that has been two-folded is fixed in a state in which the exterior sheet 7a is two-folded. That is, the end sections of the exterior sheet 7a in CD direction, which are stacked by being two-folded in the thickness direction, are welded at a position in MD direction between adjacent absorbent main bodies 3 and 3. And, the end sections are fixed in the state in which the exterior sheet 7a is two-folded. The welded part remains on the exterior sheet 7a, as a sealed end section jes (corresponding to the joined part). On the other hand, in both cases of L-size diapers and LL-size diapers, the exterior sheet 7a is in the pitch-P0 extended state. And, in the exterior sheet 7a in both cases, positions where the sealed end sections jes are to be formed are produced at the predetermined pitch P0 in MD direction. Accordingly, in both cases of the exterior sheet 7a for L-size diapers and the exterior sheet 7a for LL-size diapers, a single heat-sealing device 61 (corresponding to the processing apparatus) included in the end-section sealing unit 60 can form a sealed end section jes for each part to be a diaper 1.

That is, it is possible to share the heat-sealing device 61 in both cases of L-size diapers and LL-size diapers.

The heat-sealing device 61 includes a pair of upper and lower rolls 61u and 61d which are driven and rotated about rotational axes along CD direction while their outer circumferential surfaces facing each other.

The upper roll 61u has a sealing pattern section 61sp on its outer circumferential surface. The sealing pattern section 61sp is a protrusion and is heated. The lower roll 61d has a smooth outer circumferential surface, which is for receiving the sealing pattern section 61sp. The sealing pattern section 61sp protrudes from the outer circumferential surface of the upper roll 61u, and the protruding part has a shape corresponding to a sealed end section jes. Accordingly, when the two-folded exterior sheet 7a passes the nip between the upper and lower rolls 61u and 61d, a part of the exterior sheet 7a between the absorbent main bodies 3 and 3 which are adjacent in MD direction is heated while being pressed between a sealing pattern section 61sp and the outer circumferential surface of a lower roll 61d. Thus, a part of the exterior sheet 7a which is to be a widthwise end of each diaper 1 is melted, and the sealed end section jes is formed in the melted part.

In this example, the power source by which the upper and lower rolls 61u and 61d are driven and rotated is a servo motor (not shown). A single sealing pattern section 61sp is provided on the outer circumferential surface of the upper roll 61u. As mentioned above, exterior sheet 7a is transported being in the pitch-P0 extended state. Every time when the exterior sheet 7a passes the heat-sealing device 61 by the length of the predetermined pitch P0, the upper roll 61u rotates once. Accordingly, the sealed end sections jes are formed at the predetermined pitch P0. Consequently, in the exterior sheet 7a which is in the pitch-P0 extended state, the sealed end sections jes are formed at the predetermined pitch P0 in MD direction.

In order to form the sealed end section jes with substantially no sliding relative to the exterior sheet 7a, the rotation radius at the position of the top surface of the sealing pattern section 61sp is defined based on the predetermined pitch P0 at which the sealed end sections jes are to be formed. Similarly, the rotation radius of the outer circumferential surface of the lower roll 61d is defined based on the second pitch P2. That is, the rotation radius at the position of the sealing pattern section 61sp of the upper roll 61u, and the rotation radius of the outer circumferential surface of the lower roll 61d are set to a value obtained by dividing the predetermined pitch P0 by $2n$ (two times pi). This enables the heat-sealing device 61 to form the sealed end sections jes precisely at the predetermined pitch P0, in the exterior sheet 7a which is in the pitch-P0 extended state. Then, the exterior sheet 7a which is in the pitch-P0 extended state is transferred to the dividing unit 70 downstream in MD direction.

The extended state of the exterior sheet 7a at the time of forming the sealed end section jes is the pitch-P0 extended state as obvious in the foregoing description. The pitch-P0 extended state is a state in which a sheet being in the maximum extended state contracts. Accordingly, when forming the sealed end section jes, the basis weight (g/m²) of the exterior sheet 7a increases by an amount corresponding to the foregoing contraction. This makes it possible to increase welding strength of the sealed end section jes.

The dividing unit 70 divides at the predetermined pitch P0 the exterior sheet 7a which has been two-folded and fixed. On the other hand, in both cases of the exterior sheet 7a for L-size diapers and the exterior sheet 7a for LL-size diapers, the exterior sheet 7a remains in the pitch-P0 extended state when the exterior sheet 7a passes the dividing unit 70. In the exterior sheet 7a in the pitch-P0 extended state, parts to be a diaper 1 are lined up at the predetermined pitch P0. Accordingly, in both cases of the exterior sheet 7a for L-size diapers and the exterior sheet 7a for LL-size diapers, a single rotary cutter device 71 (corresponding to the processing apparatus) included in the dividing unit 70 can cut and separate the downstream end part of the exterior sheet 7a for each part to be a diaper 1 to produce a diaper 1. That is, it is possible to share the rotary cutter device 71 in both cases of L-size diapers and LL-size diapers.

The rotary cutter device 71 includes a pair of upper and lower rolls 71u and 71d which are driven and rotated about rotational axes along CD direction while their outer circumferential surfaces facing each other. The upper roll 71u is a cutter roll 71u having a cutter blade 71c on its outer circumferential surface, and the lower roll 71d is an anvil roll 71d having a smooth outer circumferential surface, which receives the cutter blade 71c. The cutter blade 71c is, for example, a flat blade extending along CD direction, and protrudes from the outer circumferential surface of the cutter roll 71u. When the exterior sheet 7a which is two-folded and fixed passes a nip between these upper and lower rolls 71u and 71d, the exterior sheet 7a is divided at the position of the sealed end section jes. Consequently, the downstream end part of the exterior sheet 7a is cut and separated from the sheet 7a, and the separated downstream end part becomes a diaper 1.

In this example, the power source by which the upper and lower rolls 71u and 71d are driven and rotated is a servo motor (not shown). A single cutter blade 71c is provided on the outer circumferential surface of the upper roll 71u. As mentioned above, the exterior sheet 7a is transported being in the pitch-P0 extended state. Every time when the exterior sheet 7a passes the rotary cutter device 71 by the length of the predetermined pitch P, the upper roll 71u and the lower roll 71d each rotate once. Accordingly, from the exterior sheet 7a, a single diaper 1 is divided and produced. The produced diaper 1 is transferred downstream in MD direction by a suitable transport mechanism CV such as a belt conveyor.

In order to divide the exterior sheet 7a with substantially no sliding relative to the exterior sheet 7a, the rotation radius at the position of the cutting edge of the cutter blade 71c is defined based on the predetermined pitch P0 at which the exterior sheet 7a are to be divided. Similarly, the rotation radius of the outer circumferential surface of the lower roll 71d is defined based on the predetermined pitch P0. That is, the rotation radius at the position of the cutting edge of the upper roll 71u and the rotation radius of the outer circumferential surface of the lower roll 71d are set to a value obtained by dividing the predetermined pitch P0 by $2n$ (two times pi). This enables the rotary cutter device 71 to divide the exterior sheet 7a precisely at the predetermined pitch P0, the exterior sheet 7a being in the pitch-P0 extended state.

The processing units 10 to 70 included in the manufacturing line LM are described above. The processing units 10 to 70 operate in conjunction with one another. There are two methods of the operation conjunction, for example. The one is a method in which the operation conjunction is achieved by controlling the positions of target apparatuses based on synchronization signals, and the other is a method in which the operation conjunction is achieved by controlling the speeds of target apparatuses.

The former method using synchronization signals is applied to the leg-opening forming unit 20, the absorbent-main-body attaching unit 40, the end-section sealing unit 60 and the dividing unit 70.

The synchronization signal is a signal consisting of a unit signal which corresponds to a unit part of the exterior sheet 7a which is to be a diaper 1; the unit signal is repeatedly outputted. In this example, the unit signal is a rotational angle signal having a rotational angle value of 0° to 360°. The processing units 20, 40, 60 and 70 each have a systematic unit operation which they should repeatedly perform for each unit part of the exterior sheet 7a which is to be a diaper 1. The unit operation of each of the processing units is in one-to-one correspondence with a single unit signal.

The synchronization signal is transmitted to an amplifier of each of servo motors, which are power sources of the devices 21, 41, 61 and 71 of the processing units 20, 40, 60 and 70. And, the positions of the servo motors are controlled based on the synchronization signal. Thus, each of the devices 21, 41, 61 and 71 performs its predetermined unit operation, to unit parts of the exterior sheet 7a, which are to be a diaper 1.

For example, the leg-opening forming unit 20 includes the die cutter device 21 for L-size diapers and the die cutter device 21 for LL-size diapers. In both of the die cutter devices 21, the upper and lower rolls 21u and 21d each rotate once as a unit operation according to position control, and this operation is performed for each unit signal of the synchronization signal. Thus, the leg openings 7HL are formed at the maximum pitch PLm or PLLm on the exterior sheet 7a for corresponding size diapers. In the absorbent-main-body attaching unit 40, the rotating drum 42 of the rotating-drum device 41 attaches, as a unit operation, the absorbent main body 3 to the exterior sheet 7a at the predetermined pitch P0 according to position control, and this operation is performed for each unit signal. In the end-section sealing unit 60, the upper and lower rolls 61u and 61d of the heat-sealing device each rotate once as a unit operation according to position control, and this operation is performed for each unit signal. Thus, the sealed end sections jes are formed on the exterior sheet 7a at the predetermined pitch P0. In the dividing unit 70, the upper and lower rolls 71u and 71d of the rotary cutter device 71 each rotate once as a unit operation according to position control. Thus, the exterior sheet 7a is divided at the predetermined pitch P0, to produce a diaper 1.

The synchronization signal is generated by a controller (not shown) which controls the processing units 20, 40, 60 and 70 in the manufacturing line LM, for example. The controller includes a processor and a memory, and in the memory, the program that generates the synchronization signal is stored in advance. The processor reads the program from the memory and executes it, and thereby repeatedly generates a unit signal of the synchronization signal.

For the purpose of explanation, in this example, the unit signal of the synchronization signal is a signal indicated by a rotational angle value of 0° to 360°. However, this invention is not limited thereto. For example, the unit signal of the synchronization signal may be a digital value (e.g. from 0 to 8191). Or, the synchronization signal may be generated by a suitable electric circuit, not by the processor which has read the foregoing program.

On the other hand, the latter method using speed control is applied to the exterior-sheet producing unit 10, the extension-ratio adjustment unit 30, the upstream transport mechanism CVu and the downstream transport mechanism CVd. In such a method, a reference speed value is set to the speed value (m/min.) of a core unit or the target value (m/min.) of the same. A target speed value (m/min.) is obtained by means such as multiplying the reference speed value by a suitable gain. The speed value (m/min.) of the other cooperating units is controlled so as to be close to the target speed value.

In this example, the core unit is the die cutter device 21 of the leg-opening forming unit 20. And, the reference speed value Vs is the circumferential speed value V21 (m/min.) of the lower roll 21d of the die cutter device 21. In the exterior-sheet producing unit 10, the circumferential speed value V15a of the anvil roller 15a is controlled so as to be a target speed value, which is the reference speed value Vs. In the exterior-sheet producing unit 10, concerning the transport roller 13R of the transport mechanism 13 for the low-extensible sheet 9a, the circumferential speed value V13R is controlled so as to be a target speed value, which is the reference speed value. Further, in the exterior-sheet producing unit 10, concerning the pair of nip rolls 11R and 11R of the transport mechanism 11 for the stretchable sheet 8a, each of the circumferential speed values V11R and V11R is controlled so as to be a target speed value, which is a multiplied value obtained by multiplying the reference speed value Vs by the reciprocal of the extension ratio at the time when the sheets 8 and 9 are fixed (serving as a gain; in this example, ML times for L-size diapers and MLL times for LL-size diapers).

In the extension-ratio adjustment unit 30, concerning the pair of nip rolls 31u and 31d of the upstream nip-roll mechanism 31, each circumferential speed value V31 is controlled so as to be a target speed value, which is the reference speed value Vs. Concerning the pair of nip rolls 33u and 33d of the downstream nip-roll mechanism 33, each circumferential speed value V33 is controlled so as to be a target speed value, which is a value obtained by multiplying the reference speed value Vs by a certain gain G. The gain G is a subtraction value (1−Rr) obtained by subtracting the foregoing shrinkage ratio Rr from 1, and is described above.

Taking into consideration the extended state of the exterior sheet 7a, the target speed value of each of the upstream transport mechanism CVu and the downstream transport mechanism CVd is obtained based on the foregoing reference speed value Vs. Concerning each of the transport mechanisms CVu and CVd, the circumferential speed value (m/min.) of its transport roller or its endless belt is controlled according to the target speed value. That is, concerning the upstream transport mechanism CVu transporting the exterior sheet 7a which is in the maximum extended state, the circumferential speed value of its transport roller or its endless belt is controlled so as to be a target speed value, which is the reference speed value Vs. On the other hand, concerning the downstream transport mechanism CVd transporting the exterior sheet 7a which is in the pitch-P0 extended state, its circumferential speed value is controlled so as to be a target speed value, which is a multiplied value obtained by multiplying the reference speed value Vs by the same gain G (=1−Rr) mentioned above.

Under such a control for cooperation, in the extension-ratio adjustment unit 30 of the manufacturing line LM, the exterior sheet 7a contracts in MD direction as mentioned above. But, because of variation in the stretchability of the exterior sheet 7a or the like, the contraction may cause a problem that a target position for each process, which is determined on the exterior sheet 7a, is shifted upstream or downstream in MD direction relative to an actual position at which a process by each of the processing units 40, 60 and 70 is made according to the synchronization signal.

For example, concerning a certain part of the exterior sheet 7a, its contraction is larger than expected, the exterior sheet 7a is transported in which the position of the certain part is shifted toward upstream in MD direction from its transportation position which is determined according to the synchronization signal. Consequently, a process by each of the processing units 40, 60 and 70 according to the synchronization signal is made at a position located downstream from the target position for the process, which is determined in the certain part of the exterior sheet 7a. On the other hand, the contraction is smaller than expected, the opposite of the foregoing description will happen. That is, there is generated a shifting amount, which indicates difference between the following positions: an actual position at which a process by each of the processing units 40, 60 and 70 is made according to the synchronization signal; and a target position determined on the exterior sheet 7a.

Figure 5A:
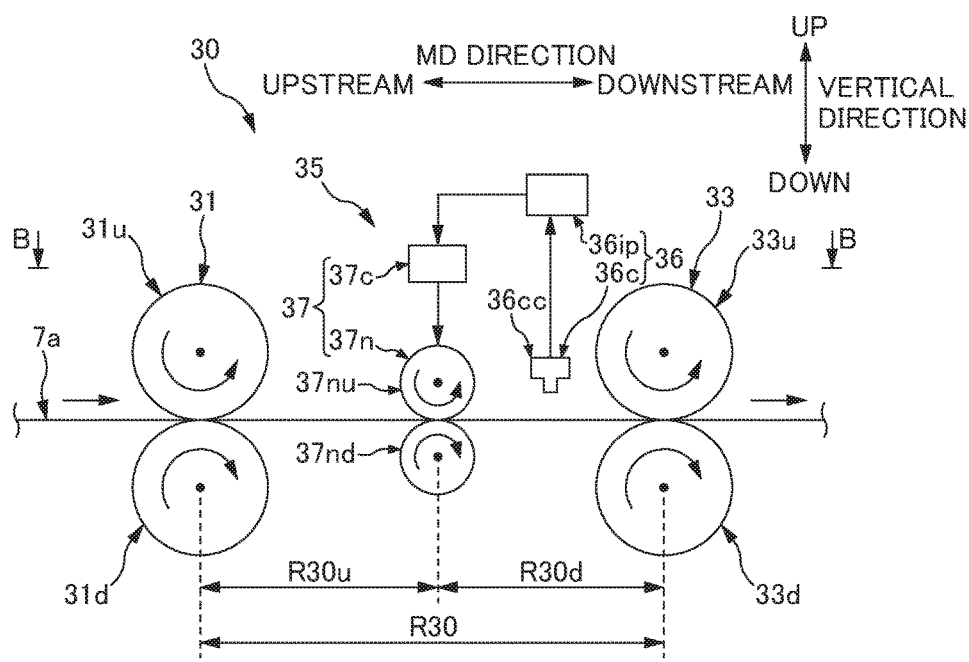
FIG. 5A is a schematic side view of an extension-ratio adjustment unit 30 including an adjustment device 35 according to the present embodiment.
Figure 5B:
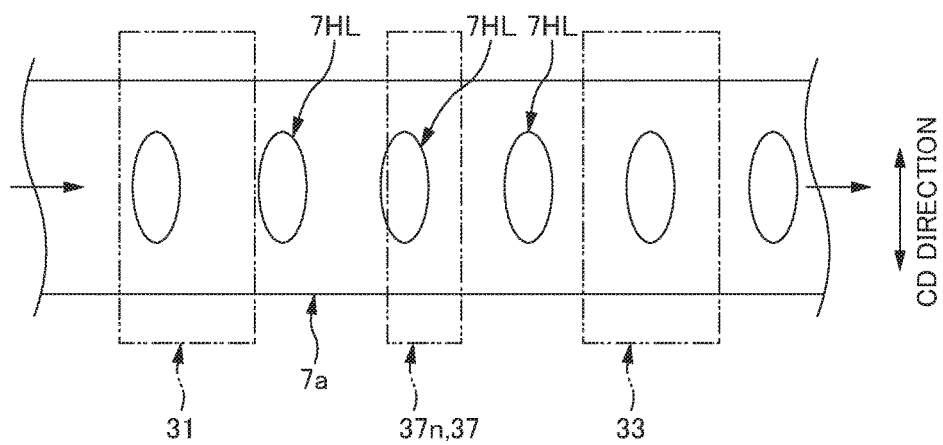
FIG. 5B is a schematic view along arrows B-B in FIG. 5A.

Accordingly, it is preferable that the adjustment device 35 which reduces the shifting amount is provided. FIG. 5A is a schematic side view of the extension-ratio adjustment unit 30 including the adjustment device 35. FIG. 5B is a schematic view along arrows B-B in FIG. 5A.

The adjustment device 35 includes a sensor 36 and an alteration device 37. The sensor 36 detects a physical reference section and outputs a detection signal. The physical reference section is a section in the exterior sheet 7a and is formed for each unit part of the exterior sheet 7a which is to be a diaper 1. The alteration device 37 alters the transportation state of the exterior sheet 7a when the exterior sheet 7a is in the transport path R30 in the extension-ratio adjustment unit 30. The alteration device 37 alters the transportation state of the exterior sheet 7a in the extension-ratio adjustment unit 30, and the alteration is performed according to the detection signal outputted from the sensor 36. And, the alteration is made so that positions in the exterior sheet 7a for processes made by the processing units 40, 60 and 70 located downstream in MD direction (that is, positions for the processes determined according to the synchronization signal) is located close to the target position which is defined on the exterior sheet 7a. The detail will be described below.

In this example, the leg opening 7HL is used as the reference section. This is because it can be considered that forming of each leg opening 7HL under a stable condition ensures a high positioning accuracy of the leg opening 7HL and that the forming of each leg opening 7HL is performed under a condition in which the 10% contraction of the exterior sheet 7a has not been made yet, that is, under a stable condition in which the exterior sheet 7a extends almost as much as possible (in the maximum extended state). In this case, in the foregoing leg-opening forming unit 20, the die cutter device 21 for L-size diapers and the die cutter device 21 for LL-size diapers respectively correspond to the "first reference-section forming apparatus" and the "second reference-section forming apparatus".

On the other hand, as shown in FIG. 5A, the alteration device 37 includes: a nip-roll mechanism 37n provided in the extension-ratio adjustment unit 30; and a controller 37c which controls the nip-roll mechanism 37n. The nip-roll mechanism 37n includes a pair of upper and lower nip rolls 37nu and 37nd which rotate respectively about rotational axes along CD direction, and the pair of nip rolls 37nu and 37nd are provided in the transport path R30 of the exterior sheet 7a, the transport path R30 being formed between the upstream nip-roll mechanism 31 and the downstream nip-roll mechanism 33 of the extension-ratio adjustment unit 30. The pair of nip rolls 37nu and 37nd are driven and rotated by obtaining driving force from a servo motor (serving as a power source) while the exterior sheet 7a is sandwiched between the outer circumferential surfaces of the nip rolls 37nu and 37nd. Thereby, the exterior sheet 7a is transferred downstream in MD direction.

The sensor 36 includes: an imaging device 36c; and an image processing device 36ip that processes image data transmitted from the imaging device 36c. The imaging device 36c includes, for example, a CCD camera, a processor and a memory. The camera 36cc images the exterior sheet 7a which is being transported between the nip-roll mechanism 37n of the alteration device 37 and the downstream nip-roll mechanism 33 in the transport path R30d.

The imaging is performed according to the foregoing synchronization signal. That is, the imaging device 36c always receives a synchronization signal, and the imaging device 36c performs the imaging when the device 36c detects that the rotational angle value of the synchronization signal matches a predetermined rotational angle value which is stored in the memory of the imaging device 36c in advance. The predetermined rotational angle value is set to such a value that the leg opening 7HL serving as the reference section is positioned within an image indicated with the image data. Every time when the rotational angle value of the synchronization signal matches the predetermined rotational angle value, the imaging device 36c performs the imaging. Accordingly, in this example, the imaging is performed for each leg opening 7HL and its image data is generated. Every time when new image data is generated, the new image data is transmitted to the image processing device 36ip.

The main body of the image processing device 36ip is a suitable computer, and includes a processor and a memory. Every time when image data is transmitted from the imaging device 36c, the image processing device 36ip performs binarization operation as an example of the image processing, according to the transmitted image data. In the binarization operation, concerning a part of the image indicated by the image data in which a leg opening 7HL is imaged, positional coordinates of the pixels of the part is obtained by extracting the pixels of the part. The detail thereof is as follow.

An image indicated by image data consists of a plurality of pixels lined up two dimensionally in X direction and in Y direction. In the image, X direction is CD direction and Y direction is MD direction, for example. The image data has color information corresponding to each pixel. In this example, since image data is a grayscale image, each pixel includes only the brightness as color information. The pixels indicating a leg opening 7HL each have lower brightness than those of the pixels indicating the exterior sheet 7a. And, in the binarization operation, a pixel having a brightness equal to or greater than a certain threshold is assigned to white image, and a pixel having a brightness less than the certain threshold is assigned to black image. This binarization operation makes it possible to extract, as black image, a part of the image in which the leg opening 7HL is imaged. The part in which the leg opening 7HL is imaged is extracted as black image, and the arithmetic average values of the positional coordinates of all pixels constituting the black image can be used as representative positional coordinates, which are representative of the positional coordinates of the pixels of the part in which the leg opening 7HL is imaged.

On the other hand, for each of an L-size diaper and an LL-size diaper, data of positional coordinates for comparison are stored in advance in the memory of the image processing device 36ip. Here, the positional coordinates for comparison indicate positional coordinates where pixels of the leg opening 7HL should be positioned in the image if the processing units 40, 60 and 70 perform processes according to the synchronization signal precisely at the predetermined target position of the exterior sheet 7a. Of the positional coordinates, the Y coordinate indicates the coordinate in MD direction. When the exterior sheet 7a for L-size diapers is transported in the manufacturing line LM, the foregoing processor is operated so as to refer the data of the comparison positional coordinates for L-size diapers. On the other hand, when the exterior sheet 7a for LL-size diapers is transported, the foregoing processor is operated so as to refer the data of the comparison positional coordinates for LL-size diapers.

Accordingly, the image processing device 36ip can calculate the shifting amount of the exterior sheet 7a in MD direction based on the difference between the followings: the value of Y coordinate of the comparison positional coordinates for the intended size; and the value of Y coordinate of the positional coordinates of the pixels of the part in which the leg opening 7HL is imaged, the positional coordinates being obtained by extracting in the binarization operation. Every time when the shifting amount is calculated, the calculated shifting amount is transmitted to the controller 37c of the alteration device 37 in the form of data (corresponding to a detection signal).

The controller 37c controls the alteration device 37 based on the foregoing data. That is, if the data indicates "the exterior sheet 7a is shifted upstream in MD direction", the controller 37c controls an amplifier of each of the servo motors of the nip rolls 37nu and 37nd of the alteration device 37. And, the circumferential speed value of the nip rolls 37nu and 37nd is set to a larger value by a certain alteration amount ΔV than the current circumferential speed value. The alteration amount ΔV of the circumferential speed value is calculated, for example, by multiplying the shifting amount by a predetermined gain. The alteration of the circumferential speed value decreases the shifting amount by which the exterior sheet 7a is shift upstream.

On the other hand, if the data indicates "the exterior sheet 7a is shifted downstream in MD direction", the controller 37c controls an amplifier of each of the servo motors of the nip rolls 37nu and 37nd of the alteration device 37. And, the circumferential speed value of the nip rolls 37nu and 37nd is set to a smaller value by a certain alteration amount ΔV than the current circumferential speed value. Also, in this case, the alteration amount ΔV of the circumferential speed value is calculated, for example, by multiplying the shifting amount by a predetermined gain. The alteration of the circumferential speed value decreases the shifting amount by which the exterior sheet 7a is shift downstream.

In this example, the alteration is performed every time when the foregoing data is transmitted to the controller 37c. Thus, adjustment for decreasing the shifting amount is made for all of the unit parts of the exterior sheet 7a each of which is to be a diaper 1. However, this invention is not limited thereto. For example, a single alteration may be performed every time when multiple times of data transmissions are made.

In this example, the controller 37c of the alteration device 37 includes an interlock regarding control of the rotations of the nip rolls 37nu and 37nd, and the interlock is in the form of a program or an electric circuit. Accordingly, the circumferential speed values of the nip rolls 37nu and 37nd of the alteration device 37 is altered between an upper limit and a lower limit; the upper limit is the circumferential speed values of the nip rolls 31u and 31d of the upstream nip-roll mechanism 31, and the lower limit is the circumferential speed values of the nip rolls 33u and 33d of the downstream nip-roll mechanism 33. This makes it possible to anticipate and avoid rotation being out of control.

Figure 6:
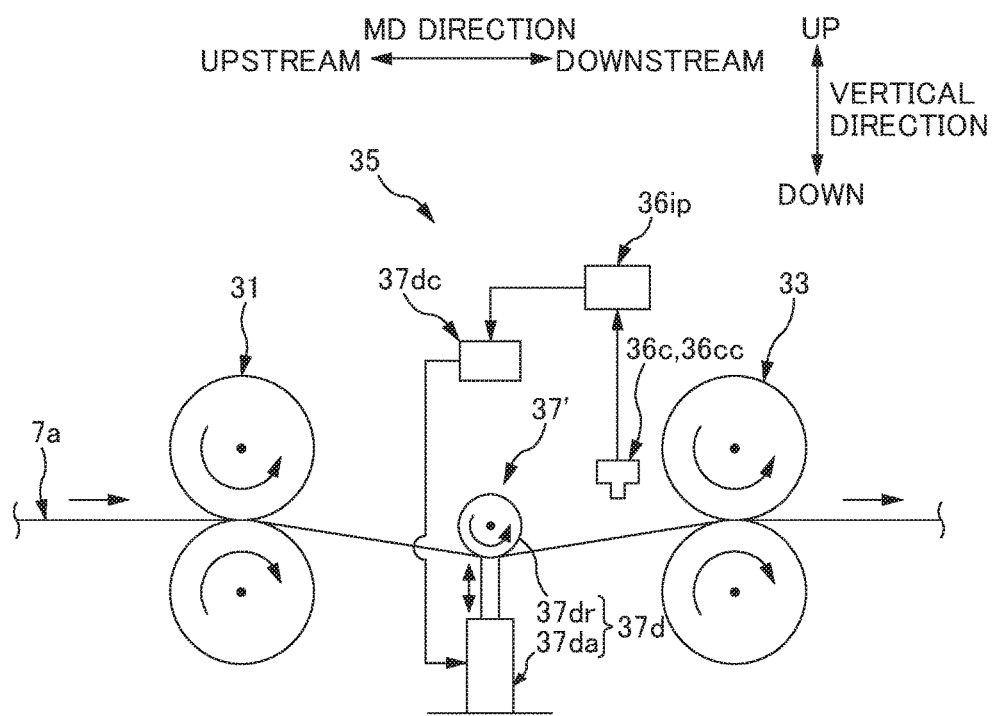
FIG. 6 is a schematic side view of a modified example 37' of an alteration device 37 included in the adjustment device 35.

FIG. 6 is a diagram illustrating a modified example 37' of the alteration device 37. In the foregoing embodiment, the alteration device 37 includes the nip-roll mechanism 37n as shown in FIG. 5A. But, the alteration device 37' in the modified example of FIG. 6 is different in that the alteration device 37' includes a dancer-roll mechanism 37d instead of the nip-roll mechanism 37n. The rest of the configuration is substantially the same as that of the foregoing embodiment. The same components as those of the foregoing embodiment will be denoted by the same reference symbols, and the description thereof is omitted.

As shown in FIG. 6, the dancer-roll mechanism 37d includes: a dancer roll 37dr and an actuator 37da. The dancer roll 37dr is capable of rotating about a rotational axis along CD direction while the exterior sheet 7a being in contact with its outer circumferential surface. The actuator 37da is, for example, a hydraulic cylinder, and the actuator 37da allows the dancer roll 37dr to reciprocate in the thickness direction of the exterior sheet 7a (up-and-down direction) while supporting the dancer roll 37dr in a rotatable manner. To the controller 37dc which controls the actuator 37da, data indicating the foregoing shifting amount is transmitted from the image processing device 36ip.

Then, the controller 37dc controls the alteration device 37' based on the foregoing data. That is, if the data indicates "the exterior sheet 7a is shifted upstream in MD direction", the controller 37dc controls the actuator 37da and moves the dancer roll 37dr upward so that a loop of the exterior sheet 7a becomes smaller. This decreases the shifting amount by which the exterior sheet 7a is shifted upstream. On the other hand, if the data indicates "the exterior sheet 7a is shifted downstream in MD direction", the controller 37dc controls the actuator 37da and moves the dancer roll 37dr downward so that a loop of the exterior sheet 7a becomes larger. This decreases the shifting amount by which the exterior sheet 7a is shifted downstream.

In the foregoing embodiment, as shown in FIG. 4A, the extension-ratio adjustment unit 30 is arranged between the leg-opening forming unit 20 and the absorbent-main-body attaching unit 40. This makes it possible to share, for both of L-size diapers and LL-size diapers, the processing devices 41, 61 and 71 of the processing units 40, 60 and 70, which are all units located downstream in MD direction from the processing unit 40. However, the arrangement position of the extension-ratio adjustment unit 30 is not limited thereto. That is, if a certain processing apparatus is required to be shared for both of L-size diapers and LL-size diapers, it is sufficient that the extension-ratio adjustment unit 30 is arranged upstream in MD direction from the unit including the certain processing apparatus. In this case, the certain processing apparatus can be shared for both of L-size diapers and LL-size diapers without any problem. For example, instead of the foregoing position, the extension-ratio adjustment unit 30 may be arranged between the absorbent-main-body attaching unit 40 and the two-folding unit 50. Or, the unit 30 may be arranged between the two-folding unit 50 and the end-section sealing unit 60, and may be arranged between the end-section sealing unit 60 and the dividing unit 70.

In addition to the area between the leg-opening forming unit 20 and the absorbent-main-body attaching unit 40, an additional extension-ratio adjustment unit 30 may be provided anywhere between the processing units 40, 50, 60 and 70. For example, additional extension-ratio adjustment units 30 may be provided respectively to the following three areas: an area between the absorbent-main-body attaching unit 40 and the two-folding unit 50; an area between the two-folding unit 50 and the end-section sealing unit 60; and an area between the end-section sealing unit 60 and the dividing unit 70. This makes it possible to set predetermined pitches P0 of each of the abovementioned four processing units 40, 50, 60 and 70 to different values. Accordingly, even if the pitches at which the four processing units 40, 50, 60 and 70 respectively performs their own processes to the exterior sheet 7a are different from one another, it is possible to share the processing devices 41, 61 and 71 of the processing units 40, 50, 60 and 70 in both cases of L-size diapers and LL-size diapers.

However, this invention is not limited thereto. For example, in the case where additional extension-ratio adjustment units 30 are provided corresponding to the four processing units 40, 50, 60 and 70 as mentioned above, the predetermined pitches P0 of all processing units 40, 50, 60 and 70 may be equal. In this case, the exterior sheet 7a is securely adjusted at each time immediately before the processing units 40, 50, 60 and 70 so that parts to be a diaper 1 are lined up at the equal predetermined pitch P0. Each of the processing units 40, 50, 60 and 70 can perform their own process at the predetermined pitch P0 to the exterior sheet 7a which has undergone the adjustment. Accordingly, each of the processing units 40, 50, 60 and 70 can perform its own processes to exterior sheet 7a for each part to be a diaper 1 with high positioning accuracy.

Depending on the case, the following configuration may be employed. That is, if the extension-ratio adjustment unit 30 is provided for each of four processing units 40, 50, 60 and 70 as mentioned above, the predetermined pitch P0 may be different between at least two of these units. In this case, it is possible to individually adjust the predetermined pitch of each of at least the two units. This makes it possible to perform a process to the exterior sheet 7a at an optimal pitch. This configuration can be generally described as follow: "if a plurality of mechanism units each of which is composed of the extension-ratio adjustment unit 30 and the downstream transport mechanism CVd are included and lined up in MD direction, the predetermined pitches P0 may be different between at least two mechanism units of the plurality of mechanism units".

In some cases, an additional extension-ratio adjustment unit 30 may be provided to an area which is selected among the foregoing three areas. Or, additional extension-ratio adjustment units 30 may be provided respectively to two areas which are selected among the foregoing three areas.

In the foregoing manufacturing line LM, as shown in FIG. 4A, the absorbent-main-body attaching unit 40 is placed downstream in MD direction from the leg-opening forming unit 20. However, this invention is not limited thereto. For example, as shown in the modified example LM' of the manufacturing line LM illustrated in FIG. 7, the leg-opening forming unit 20 may be arranged downstream in MD direction from the absorbent-main-body attaching unit 40. In this case, however, the leg opening 7HL cannot be used as a reference section which the sensor 36 of the adjustment device 35 should detect, and this is because the leg-opening forming unit 20 is located downstream from the adjustment device 35 of the extension-ratio adjustment unit 30. Accordingly, in this case, it is necessary to provide another physical reference section with the exterior sheet 7a. The detail thereof is as follow.

Figure 7:
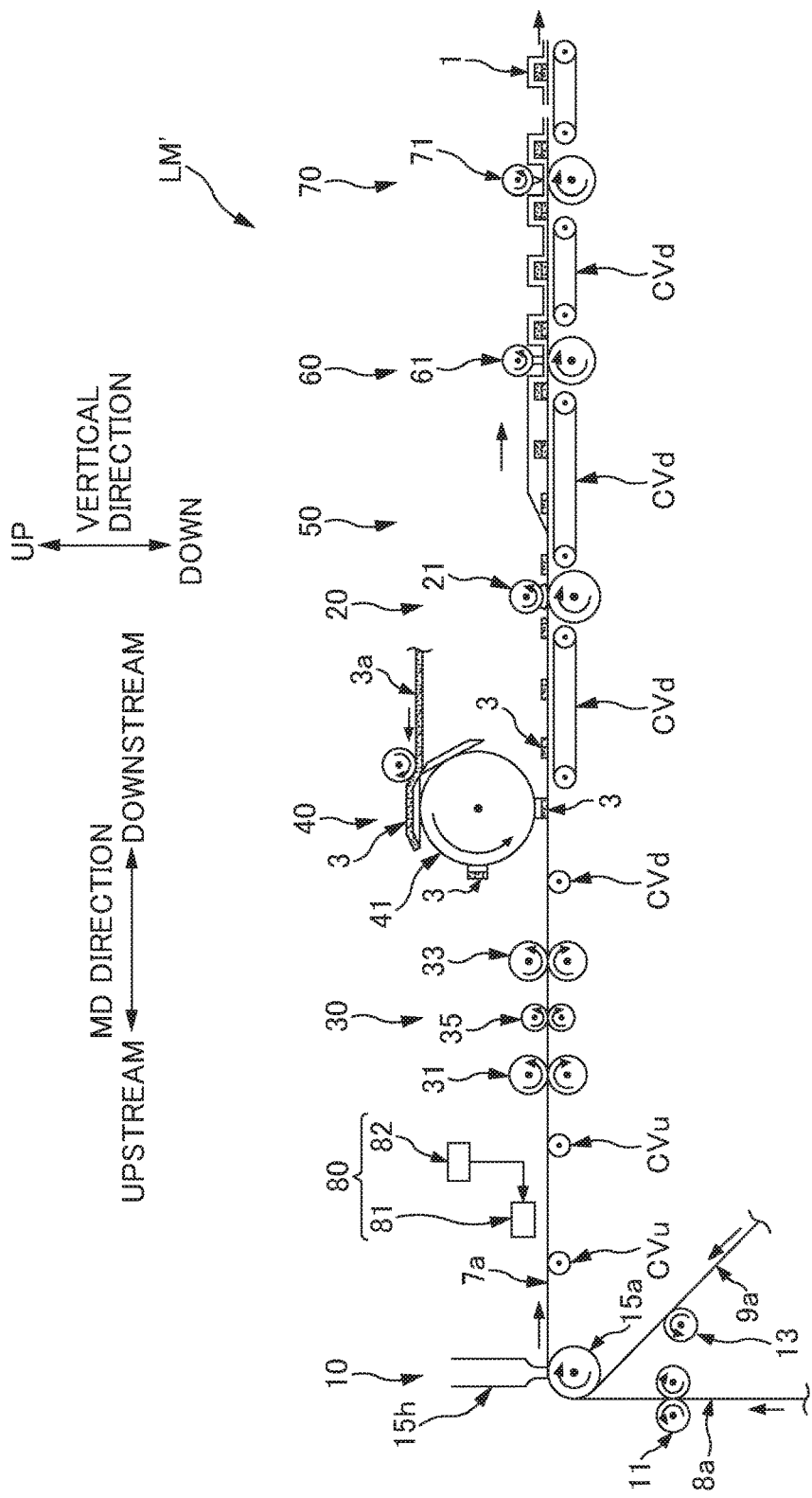
FIG. 7 is a schematic side view of a manufacturing line LM' of a modified example in which a leg-opening forming unit 20 is provided downstream in MD direction from an absorbent-main-body attaching unit 40.

In the example of FIG. 7, a printing unit 80 which prints a mark as a reference section (corresponding to the reference-section forming apparatus) is arranged between the exterior-sheet producing unit 10 and the extension-ratio adjustment unit 30. The printing unit 80 includes a suitable printer 81 and a controller 82 which controls the printer 81. The printer 81 is located in a transport path between the exterior-sheet producing unit 10 and the extension-ratio adjustment unit 30, and prints a mark onto the exterior sheet 7a. Here, the printing is performed according to the foregoing synchronization signal. That is, every time when the rotational angle value of the synchronization signal matches the predetermined rotational angle value, the controller 82 outputs a print instruction signal to the printer 81 so that the printer 81 prints a mark. Thus, the printer 81 prints a mark onto each unit part of the exterior sheet 7a which is to be a diaper 1. Since such a mark is printed according to the synchronization signal as mentioned above, the printing is made with a high accuracy at the predetermined position of the unit part which is to be a diaper 1. Accordingly, the mark can effectively serve as a reference section which indicates a specific position in the exterior sheet 7a.

In such a configuration, the leg-opening forming unit 20 is located downstream in MD direction from the extension-ratio adjustment unit 30. Accordingly, the transportation state of the exterior sheet 7a in the extension-ratio adjustment unit 30 is adjusted according to the mark, and thereby parts of the exterior sheet 7a to be the leg opening 7HL can be transferred to the die cutter device 21 of the leg-opening forming unit 20 with high positioning accuracy. This makes it possible to form the leg opening 7HL with high positioning accuracy.

Further, in such a configuration, the exterior sheet 7a in the pitch-P0 extended state can be transported to the leg-opening forming unit 20. Accordingly, the single die cutter device 21, which forms the leg opening 7HL, can be shared for both of L-size diapers and LL-size diapers.

A type of printer applicable to the printer 81 is not particularly limited as long as the printer can print a mark. For example, an inkjet printer, a flexographic printer, a screen printer and the like are available. A type of the mark is not particularly limited either. For example, the mark may be a pattern, a character, a picture, a symbol or the like.

In the example of FIG. 7, a mark is printed on the stretchable sheet 8a of the exterior sheet 7a. However, this invention is not limited thereto. That is, a mark may be printed on the low-extensible sheet 9a. In this case, the mark can serve as a more accurate reference section. That is, even if an unexpectedly great tension is exerted during transportation after printing, the low-extensible sheet 9a do not greatly deform and can resist the tension due to its low extensibility. This can prevent such a phenomenon as distortion of the mark. Consequently, the mark can effectively serve as an exact reference section.

Other Embodiments

While the embodiment according to the invention are described above, the foregoing embodiment is provided for facilitating the understanding of the invention, and is not to be interpreted as limiting the invention. As a matter of course, the invention can be altered and improved without departing from the gist thereof and the invention includes equivalent thereof. For example, the invention can be altered as described below.

In the foregoing embodiment, the first stretchable sheet-like member in which the parts to be the absorbent article are lined up at the first pitch is exemplified by the exterior sheet 7*a* for L-size diapers, and the second stretchable sheet-like member in which the parts to be the absorbent article are lined up at the second pitch is exemplified by the exterior sheet 7*a* for LL-size diapers. However, this invention is not limited thereto. For example, an exterior sheet 7*a* for S-size diapers, an exterior sheet 7*a* for M-size diapers and an exterior sheet 7*a* for L-size diapers may be processed in the manufacturing line LM of the foregoing embodiment.

In the foregoing embodiment, in both of the exterior sheet 7*a* for L-size diapers and the exterior sheet 7*a* for LL-size diapers, the pitch PL and the pitch PLL before adjustment to the pitch-P0 extended state are respectively the maximum pitch PLm and the maximum pitch PLLm. Accordingly, the extension-ratio adjustment unit 30 adjusts the pitch to the predetermined pitch P0 by means of contraction only. However, this invention is not limited thereto. That is, if the exterior sheet 7*a* can extend in the adjustment process, the adjustment to the predetermined pitch P0 may be performed by the extension of the exterior sheet 7*a*. But, since such an extension of the exterior sheet 7*a* is accompanied with danger of breakage, it is preferable to use contraction only.

In the foregoing embodiment, in the extension-ratio adjustment unit 30, the extension ratio for L-size diapers and the extension ratio for LL-size diapers are changed in order to adjust to the predetermined pitch P0. However, this invention is not limited thereto. For example, the extension ratio may be maintained without change if the maximum extension length DL of the exterior sheet 7*a* for L-size diapers, the smaller maximum extension length, is equal to the predetermined pitch P0. That is, the concept of "adjust" according to the invention includes not only changing the extension ratio but also maintaining the extension ratio. In this case, in the extension-ratio adjustment unit 30, the exterior sheet 7*a* for LL-size diapers contracts, but the exterior sheet 7*a* for L-size diapers does not contract.

In the foregoing embodiment, the exterior sheet 7*a* for L-size diapers and the exterior sheet 7*a* for LL-size diapers have the same dimension in CD direction. However, this invention is not limited thereto. For example, the exterior sheet 7*a* for LL-size diapers may have a larger dimension in CD direction than that of the exterior sheet 7*a* for L-size diapers.

In the foregoing embodiment, the absorbent main body 3 is identical for both of L-size diapers and LL-size diapers. However, this invention is not limited thereto. For example, an absorbent main body 3 for LL-size diapers may have a larger planar size than that of an absorbent main body 3 for L-size diapers. In addition, the absorbent main body 3 for LL-size diapers may have a larger thickness than that of the absorbent main body 3 for L-size diapers.

In the foregoing embodiment, a configuration including the imaging device 36*c* and the image processing device 36*ip* is provided as an example of the sensor 36 that detects the reference sections. However, this invention is not limited thereto. For example, a configuration including a phototube and a suitable controller may be used as a sensor that detects the reference sections. In this case, the controller can obtain the shifting amount of the exterior sheet 7*a* in MD direction, based on the difference between the following rotational angle values; one is the rotational angle value of a synchronization signal at the time when the phototube detects passing of the reference section, and the other one is a predetermined rotational angle value which is stored in advance for comparison in a memory of the controller. The predetermined rotational angle values for comparison are respectively prepared for L-size diapers and for LL-size diapers, and are stored in the memory.

In the foregoing embodiment, as shown in FIG. 5A, the sensor 36 that detects the reference sections is configured to detect the leg opening 7HL (serving as the reference section) during the period when the exterior sheet 7*a* is moving in the transport path R30*d* between the nip-roll mechanism 37*n* of the adjustment device 35 and the downstream nip-roll mechanism 33 of the extension-ratio adjustment unit 30. However, this invention is not limited thereto. For example, the sensor 36 may detect the leg opening 7HL during the period when the exterior sheet 7*a* is moving in the transport path R30*u* between the upstream nip-roll mechanism 31 of the extension-ratio adjustment unit 30 and the nip-roll mechanism 37*n* of the adjustment device 35. Or, as shown in FIG. 4A, the sensor 36 may detect the leg opening 7HL during the period when the exterior sheet 7*a* is moving in the transport path between the downstream nip-roll mechanism 33 of the extension-ratio adjustment unit 30 and the absorbent-main-body attaching unit 40. That is, the sensor 36 can be used without any problem as long as the sensor 36 is arranged so as to detect the reference section during the time period from the contraction of the exterior sheet 7*a* in the extension-ratio adjustment unit 30 till the attachment of the absorbent main body 3. However, the foregoing configuration does not mean that the sensor 36 is not arranged so as to detect the reference section during the attachment process of the absorbent main body 3 or later. That is, even if the detection is performed during the attachment or later, the sensor 36 can be used without any serious problem. Accordingly, broadly speaking, it is sufficient that the sensor 36 is arranged so as to detect the reference section during the contraction in the extension-ratio adjustment unit 30 or later.

Figure 8:
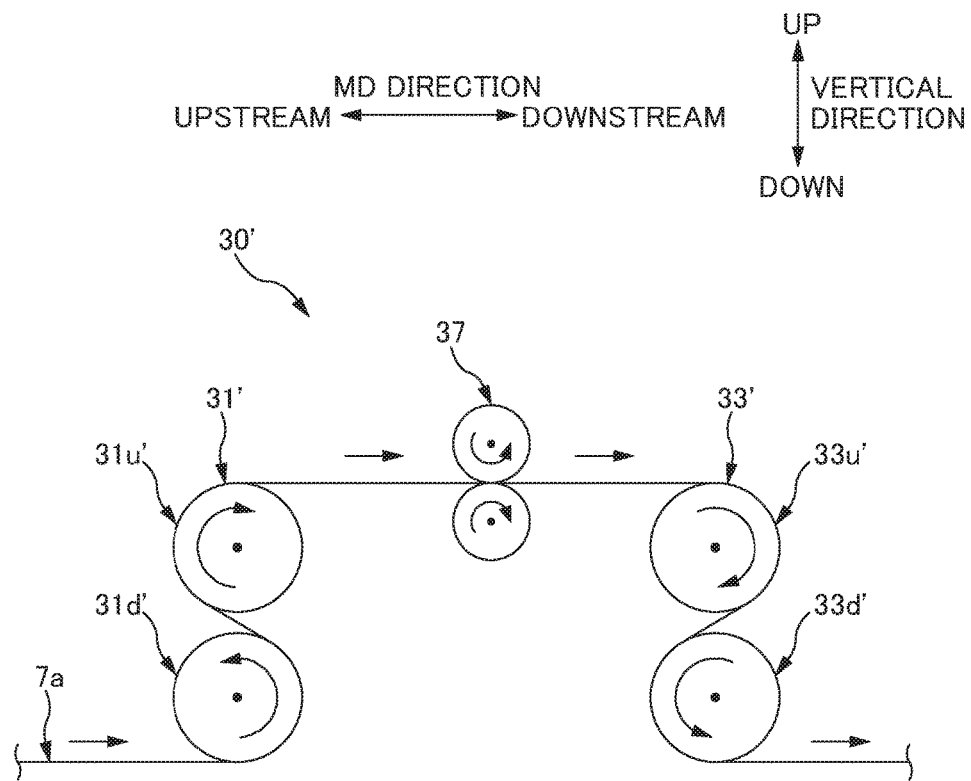
FIG. 8 is a schematic side view of a modified example 30' of an extension-ratio adjustment unit 30.

In the foregoing embodiment, as a mechanism in which the exterior sheet 7*a* in the first extended state contracts, the extension-ratio adjustment unit 30 has a pair of nip-roll mechanisms 31 and 33 as shown in FIG. 5A. However, the invention is not limited thereto as long as a mechanism in which the exterior sheet 7*a* is able to contract. For example, instead of the pair of nip-roll mechanisms 31 and 33, a pair of S-shaped-winding roll mechanisms 31' and 33' shown in FIG. 8 may be provided. That is, each S-shaped-winding roll mechanism 31' (33') includes a pair of rolls 31*u*' and 31*u*' (33*u*' and 33*d*') which are driven and rotated about rotational axes along CD direction while their outer circumferential surfaces facing each other. The exterior sheet 7*a* is wound around the pair of rolls 31*u*' and 31*d*' (33*u*' and 33*d*') in an S shapes. In such a configuration, the outer circumferential surfaces of the rolls 31*u*' and 31*d*' (33*u*' and 33*d*') can hold the exterior sheet 7*a* with substantially no relative sliding. Since these rolls 31*u*' and 31*d*' (33*u*' and 33*d*') are driven and rotated, the exterior sheet 7*a* can be transported at a conveying speed which is equal to the circumferential speed values of the rolls 31*u*' and 31*d*' (33*u*' and 33*d*'). The S-shaped-winding roll mechanisms 31' and 33' can therefore be used instead of the foregoing nip-roll mechanisms 31 and 33. In the example of FIG. 8, both of the nip-roll mechanisms 31 and 33 are replaced with the S-shaped-winding roll mechanisms 31' and 33'. In some cases, either one of the nip-roll mechanisms 31 and 33 may be replaced with the S-shaped-winding roll mechanism 31 (or 33).

Figure 9:
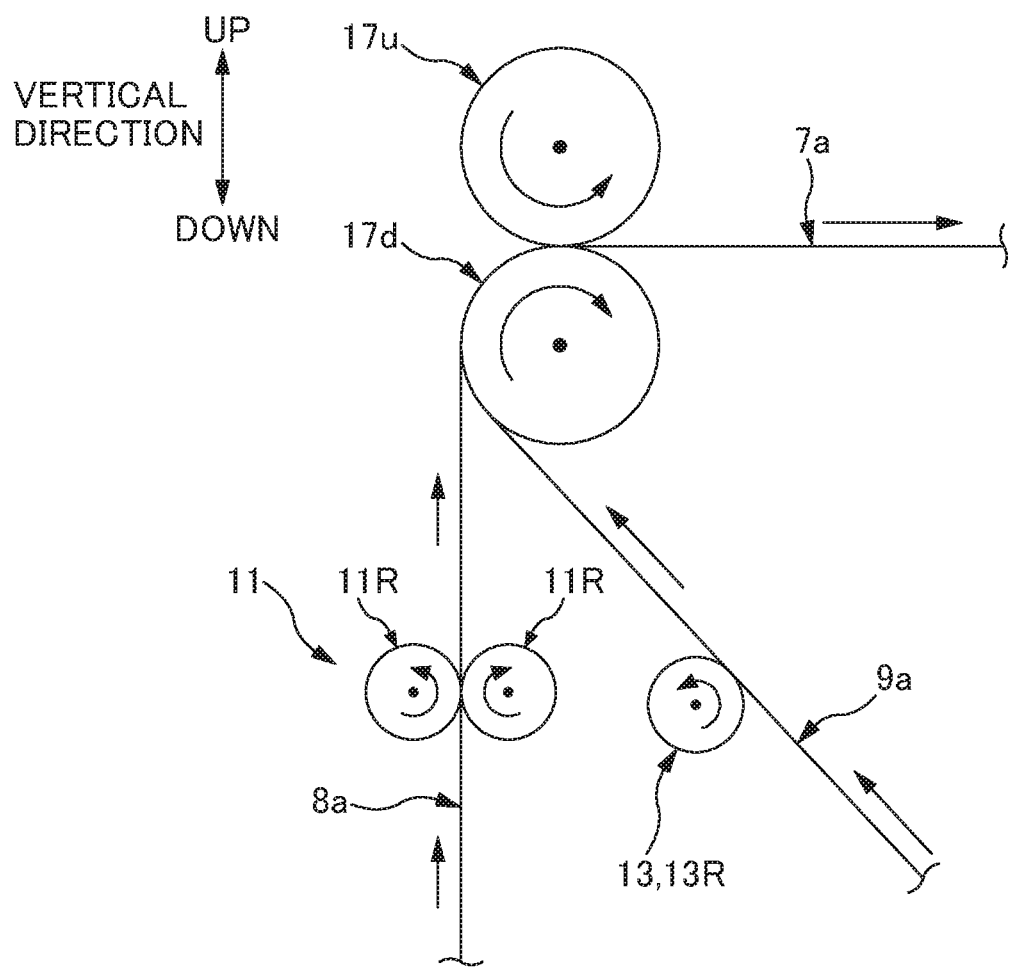
FIG. 9 is a schematic side view of a configuration in which a heat-sealing device or a compression-bonding device is provided instead of an ultrasonic welding device 15 of an exterior-sheet producing unit 10.

In the foregoing embodiment, as shown in FIG. 4A, the stretchable sheet 8*a* and the low-extensible sheet 9*a* are fixed to each other in the exterior-sheet producing unit 10, and the fixing is performed by the ultrasonic welding device 15. However, this invention is not limited thereto. For example, as shown in FIG. 9, instead of the ultrasonic welding device 15, a heat-sealing device or a compression-bonding device may be used. The heat-sealing device and the compression-bonding device have a configuration similar to each other. That is, the main difference between their configurations is whether their rolls are heated or not. Both of the devices include a pair of upper and lower rolls 17*u* and 17*d* which are driven and rotated about rotational axes along CD direction, and each of the rolls 17*u* and 17*d* rotates at the same circumferential speed value as the circumferential speed value V15*a* of the anvil roller 15*a* of the foregoing ultrasonic welding device 15. In such a configuration, the stretchable sheet 8*a* and the low-extensible sheet 9*a* which are stacked passes the nip between the rolls 17*u* and 17*d* while the stretchable sheet 8*a* extending till the reference extended state and the low-extensible sheet 9*a* being extended and tightened. When passing the nip, both sheets 8*a* and 9*a* are pressed by these rolls 17*u* and 17*d* between the rolls. Thus, the sheets 8*a* and 9*a* are be welded or pressed, and are fixed in an integrated manner. In a case of pressing, adhesive such as hot-melt adhesive may be applied, before the pressing, onto at least either one of the stretchable sheet 8*a* and the low-extensible sheet 9*a* in a certain applying pattern.

In the foregoing embodiment, in the leg-opening forming unit 20, the die cutter devices 21 for L-size diapers and for LL-size diapers each include the single cutter blade 21*c* on the outer circumferential surface of the upper roll 21*u*. However, this invention is not limited thereto. That is, a plurality of the cutter blades 21*c* may be provided on the outer circumferential surface of the upper roll 21*u*. In this case, it is preferable that the plurality of cutter blades 21*c* are arranged at a uniform pitch in the rotating direction of the upper roll 21*u*. It is more preferable that the length of the circular tracks traced by the cutting edge of the cutter blade 21*c* as a result of the rotation of the upper roll 21*u* is an integral multiple of the corresponding pitch PLm or pitch PLLm. In such a configuration, the die-cutting by the cutter blade 21*c* can be stabilized. The same is also true for the heat-sealing device 61 of the end-section sealing unit 60, and is also true for the rotary cutter device 71 of the dividing unit 70. That is, in the foregoing embodiment, the end-section sealing unit 60 also includes the single sealing pattern section 61*sp* in the upper roll 61*u*, and the dividing unit 70 includes the single cutter blade 71*c* in the upper roll 71*u*. However, this invention is not limited thereto. The sealing pattern section 61*sp* which traces a circular track as mentioned above may be provided in the rotating direction at a uniform pitch, and also the cutter blade 71*c* which traces a circular track as mentioned above may be provided in the rotating direction at a uniform pitch.

In the foregoing embodiment, in the exterior-sheet producing unit 10, the stretchable sheet 8*a* is fixed to the low-extensible sheet 9*a*. But, a single or a plurality of additional sheet(s) may be fixed together. The additional sheet(s) to be fixed may be a stretchable sheet, or may be a low-extensible sheet. The sheet(s) may be made of nonwoven fabric, woven fabric or film.

REFERENCE SIGNS LIST

1 disposable diaper (absorbent article),
3 absorbent main body, 3*e* end,
3*a* continuous body of absorbent main body,
3*c* absorbent core,
4 top sheet, 4*e*L projecting part,
5 leak-proof sheet, 5*e*L projecting part, 5*e*W projecting part,
7 exterior sheet, 7HL leg opening,
7*f* ventral part, 7*c* crotch part, 7*b* dorsal part, 7*e*W end
7*a* continuous sheet of exterior sheet (exterior sheet, stretchable sheet-like member),
8 inner-layer sheet (stretchable sheet),
8*a* continuous sheet of stretchable sheet (stretchable sheet),
9 outer-layer sheet (low-extensible sheet),
9*a* continuous sheet of low-extensible sheet (low-extensible sheet),
10 exterior-sheet producing unit,
11 transport mechanism for stretchable sheet, 11R nip roll
13 transport mechanism for low-extensible sheet, 13R transport roller,
15 ultrasonic welding device, 15*a* anvil roller, 15*h* horn,
17*u* upper roll, 17*d* lower roll,
20 leg-opening forming unit,
21 die cutter device (first reference-section forming apparatus, second reference-section forming apparatus),
21*c* cutter blade,
21*u* cutter roll, 21*d* anvil roll,
30 extension-ratio adjustment unit (extension-ratio adjustment mechanism),
30' extension-ratio adjustment unit (extension-ratio adjustment mechanism),
31 upstream nip-roll mechanism, 31*u* upper nip roll, 31*d* lower nip roll,
33 downstream nip-roll mechanism, 33*u* upper nip roll, 33*d* lower nip roll,
31' S-shaped-winding roll mechanism, 31*u*' upper roll, 31*d*' lower roll,
33' S-shaped-winding roll mechanism, 33*u*' upper roll, 33*d*' lower roll,
35 adjustment device,
36 sensor, 36*c* imaging device, 36*cc* camera, 36*ip* image processing device,
37 alteration device, 37' alteration device,
37*n* nip-roll mechanism, 37*nu* upper nip roll, 37*nd* lower nip roll,
37*c* controller,
37*d* dancer-roll mechanism, 37*da* actuator, 37*dc* controller,
37*dr* dancer roll,
40 absorbent-main-body attaching unit,
41 rotating-drum device (processing apparatus), 42 rotating drum,
43 holding pad,
45 cutter apparatus,
50 two-folded unit,
60 end-section sealing unit,
61 heat-sealing device (processing apparatus), 61*u* upper roll, 61*d* lower roll,
61*sp* sealing pattern section,
70 dividing unit,
71 rotary cutter device (processing apparatus), 71*a* rotary cutter device,
71*c* cutter blade, 71*ca* cutter blade,
71*u* upper roll (cutter roll), 71*d* lower roll (anvil roll),
71*ua* roll,
80 printing unit (reference-section forming apparatus), 81 printer,
82 controller,
HB waist opening, HL leg opening,
S1 first position, S2 second position,
j joined part, jL longitudinal band-like part, jW widthwise band-like part, jC joined part, LM manufacturing line, LM' manufacturing line, LMa manufacturing line,
R30 transport path,
R30u transport path, R30d transport path,
CV transport mechanism,
CVu upstream transport mechanism, CVd downstream transport mechanism,
R30 transport path, R30u transport path, R30d transport path,

The invention claimed is:

1. A manufacturing apparatus for manufacturing an absorbent article by performing a certain process to a stretchable sheet-like member associated with the absorbent article,
the stretchable sheet-like member continuing along a transporting direction,
the apparatus comprising:
an upstream transport mechanism that transports the stretchable sheet-like member along the transporting direction;
a downstream transport mechanism
that is located downstream in the transporting direction from the upstream transport mechanism, and
that transports the stretchable sheet-like member along the transporting direction;
an extension-ratio adjustment mechanism
that is located between the upstream transport mechanism and the downstream transport mechanism, and
that adjusts an extension ratio at which the stretchable sheet-like member extends in the transporting direction; and
a processing apparatus that performs the certain process to the stretchable sheet-like member that is being transported by the downstream transport mechanism,
when the upstream transport mechanism transports a first stretchable sheet-like member in which parts to be the absorbent article are lined up at a first pitch in the transporting direction,
the extension-ratio adjustment mechanism adjusting an extension ratio of the first stretchable sheet-like member so that the parts to be the absorbent article are lined up at a predetermined pitch, and
the extension-ratio adjustment mechanism transferring the first stretchable sheet-like member to the downstream transport mechanism, and
when the upstream transport mechanism transports a second stretchable sheet-like member in which the parts to be the absorbent article are lined up at a second pitch in the transporting direction, the second pitch being different from the first pitch,
the extension-ratio adjustment mechanism adjusting an extension ratio of the second stretchable sheet-like member so that the parts to be the absorbent article are lined up at the predetermined pitch, and
the extension-ratio adjustment mechanism transferring the second stretchable sheet-like member to the downstream transport mechanism.

2. A manufacturing apparatus for an absorbent article according to claim 1, wherein
of the first stretchable sheet-like member and the second stretchable sheet-like member,
to either one stretchable sheet-like member that is being transported by the downstream transport mechanism,
the processing apparatus performs the certain process at the predetermined pitch.

3. A manufacturing apparatus for an absorbent article according to claim 2, wherein
the processing apparatus attaches an absorbent main body to the stretchable sheet-like member at the predetermined pitch,
the absorbent main body is a component that should be provided to each absorbent article and absorbs liquid, and
the attaching is performed as the certain process.

4. A manufacturing apparatus for an absorbent article according to claim 2, wherein
before the stretchable sheet-like member is transported to the processing apparatus,
the stretchable sheet-like member is two-folded in a CD direction intersecting the transporting direction, and
in the processing apparatus, the stretchable sheet-like member is fixed in a state in which the stretchable sheet-like member is two-folded,
the fixing being performed by forming joined parts at the predetermined pitch in the stretchable sheet-like member that has been two-folded,
the forming being performed as the certain process.

5. A manufacturing apparatus for an absorbent article according to claim 2, wherein
before the stretchable sheet-like member is transported to the processing apparatus,
the stretchable sheet-like member is two-folded in a CD direction intersecting the transporting direction, and is fixed in a state in which the stretchable sheet-like member is two-folded, and
the processing apparatus produces the absorbent article,
the producing being performed by cutting at the predetermined pitch the stretchable sheet-like member that has been two-folded,
the cutting being performed as the certain process.

6. A manufacturing apparatus for an absorbent article according to claim 1, wherein
of the first stretchable sheet-like member and the second stretchable sheet-like member,
either one stretchable sheet-like member that is being transported by the upstream transport mechanism is in a state in which the stretchable sheet-like member extends in the transporting direction,
the manufacturing apparatus further comprises
a reference-section forming apparatus that forms a physical reference section in the stretchable sheet-like member,
the stretchable sheet-like member being in the extending state and being transported by the upstream transport mechanism, and
the extension-ratio adjustment mechanism includes:
a transport path in which the stretchable sheet-like member is transported;
a sensor
that detects the reference section after the extension ratio has been adjusted in the extension-ratio adjustment mechanism and
that outputs a detection signal; and
a transportation-state alteration device that alters a transportation state of the stretchable sheet-like member in the transport path so that a position in the stretchable sheet-like member for the certain process is located close to a target position for the certain process,
the alteration being performed according to the detection signal of the sensor.

7. A manufacturing apparatus for an absorbent article according to claim 6, wherein
the manufacturing apparatus further comprises:

a first reference-section forming apparatus that forms leg openings at the first pitch as the reference section in the first stretchable sheet-like member in which the parts to be the absorbent article are lined up at the first pitch in the transporting direction,
the leg openings being associated with the absorbent article; and
a second reference-section forming apparatus that forms leg openings at the second pitch as the reference section in the second stretchable sheet-like member in which the parts to be the absorbent article are lined up at the second pitch in the transporting direction,
the leg openings being associated with the absorbent article.

8. A manufacturing apparatus for an absorbent article according to claim 1, wherein
the predetermined pitch is smaller than the first pitch and is smaller than the second pitch.

9. A manufacturing apparatus for an absorbent article according to claim 1, wherein
the manufacturing apparatus further comprises
a plurality of mechanism units each of which is composed of the extension-ratio adjustment mechanism and the downstream transport mechanism,
the plurality of mechanism units being lined up in the transporting direction, and
the predetermined pitches of all of the plurality of mechanism units are identical.

10. A manufacturing method for manufacturing an absorbent article by performing a certain process to a stretchable sheet-like member associated with the absorbent article,
the stretchable sheet-like member continuing along a transporting direction,
the method comprising:
transporting the stretchable sheet-like member by an upstream transport mechanism along the transporting direction;
transporting the stretchable sheet-like member by a downstream transport mechanism along the transporting direction,
the downstream transport mechanism being located downstream in the transporting direction from the upstream transport mechanism;
adjusting by an extension-ratio adjustment mechanism an extension ratio at which the stretchable sheet-like member extends in the transporting direction,
the extension-ratio adjustment mechanism being located between the upstream transport mechanism and the downstream transport mechanism; and
performing the certain process by a processing apparatus to the stretchable sheet-like member that is being transported by the downstream transport mechanism, wherein
when the upstream transport mechanism transports a first stretchable sheet-like member in which parts to be the absorbent article are lined up at a first pitch in the transporting direction,
in the adjusting, an extension ratio of the first stretchable sheet-like member is adjusted so that the parts to be the absorbent article are lined up at a predetermined pitch, and
the first stretchable sheet-like member is transferred to the downstream transport mechanism, and
when the upstream transport mechanism transports a second stretchable sheet-like member in which parts to be the absorbent article are lined up at a second pitch in the transporting direction, the second pitch being different from the first pitch,
in the adjusting, an extension ratio of the second stretchable sheet-like member is adjusted so that the parts to be the absorbent article are lined up at the predetermined pitch, and
the second stretchable sheet-like member is transferred to the downstream transport mechanism.

11. A manufacturing apparatus for an absorbent article according to claim 2, wherein
of the first stretchable sheet-like member and the second stretchable sheet-like member,
either one stretchable sheet-like member that is being transported by the upstream transport mechanism is in a state in which the stretchable sheet-like member extends in the transporting direction,
the manufacturing apparatus further comprises
a reference-section forming apparatus that forms a physical reference section in the stretchable sheet-like member,
the stretchable sheet-like member being in the extending state and being transported by the upstream transport mechanism, and
the extension-ratio adjustment mechanism includes:
a transport path in which the stretchable sheet-like member is transported;
a sensor
that detects the reference section after the extension ratio has been adjusted in the extension-ratio adjustment mechanism and
that outputs a detection signal; and
a transportation-state alteration device that alters a transportation state of the stretchable sheet-like member in the transport path so that a position in the stretchable sheet-like member for the certain process is located close to a target position for the certain process,
the alteration being performed according to the detection signal of the sensor.

12. A manufacturing apparatus for an absorbent article according to claim 3, wherein
of the first stretchable sheet-like member and the second stretchable sheet-like member,
either one stretchable sheet-like member that is being transported by the upstream transport mechanism is in a state in which the stretchable sheet-like member extends in the transporting direction,
the manufacturing apparatus further comprises
a reference-section forming apparatus that forms a physical reference section in the stretchable sheet-like member,
the stretchable sheet-like member being in the extending state and being transported by the upstream transport mechanism, and
the extension-ratio adjustment mechanism includes:
a transport path in which the stretchable sheet-like member is transported;
a sensor
that detects the reference section after the extension ratio has been adjusted in the extension-ratio adjustment mechanism and
that outputs a detection signal; and
a transportation-state alteration device that alters a transportation state of the stretchable sheet-like member in the transport path so that a position in the stretchable sheet-like member for the certain process is located close to a target position for the certain process,
the alteration being performed according to the detection signal of the sensor.

13. A manufacturing apparatus for an absorbent article according to claim 4, wherein
of the first stretchable sheet-like member and the second stretchable sheet-like member,
either one stretchable sheet-like member that is being transported by the upstream transport mechanism is in a state in which the stretchable sheet-like member extends in the transporting direction,
the manufacturing apparatus further comprises
a reference-section forming apparatus that forms a physical reference section in the stretchable sheet-like member,
the stretchable sheet-like member being in the extending state and being transported by the upstream transport mechanism, and
the extension-ratio adjustment mechanism includes:
a transport path in which the stretchable sheet-like member is transported;
a sensor
that detects the reference section after the extension ratio has been adjusted in the extension-ratio adjustment mechanism and
that outputs a detection signal; and
a transportation-state alteration device that alters a transportation state of the stretchable sheet-like member in the transport path so that a position in the stretchable sheet-like member for the certain process is located close to a target position for the certain process,
the alteration being performed according to the detection signal of the sensor.

14. A manufacturing apparatus for an absorbent article according to claim 5, wherein
of the first stretchable sheet-like member and the second stretchable sheet-like member,
either one stretchable sheet-like member that is being transported by the upstream transport mechanism is in a state in which the stretchable sheet-like member extends in the transporting direction,
the manufacturing apparatus further comprises
a reference-section forming apparatus that forms a physical reference section in the stretchable sheet-like member,
the stretchable sheet-like member being in the extending state and being transported by the upstream transport mechanism, and
the extension-ratio adjustment mechanism includes:
a transport path in which the stretchable sheet-like member is transported;
a sensor
that detects the reference section after the extension ratio has been adjusted in the extension-ratio adjustment mechanism and
that outputs a detection signal; and
a transportation-state alteration device that alters a transportation state of the stretchable sheet-like member in the transport path so that a position in the stretchable sheet-like member for the certain process is located close to a target position for the certain process,
the alteration being performed according to the detection signal of the sensor.

15. A manufacturing apparatus for an absorbent article according to claim 2, wherein
the predetermined pitch is smaller than the first pitch and is smaller than the second pitch.

16. A manufacturing apparatus for an absorbent article according to claim 3, wherein
the predetermined pitch is smaller than the first pitch and is smaller than the second pitch.

17. A manufacturing apparatus for an absorbent article according to claim 4, wherein
the predetermined pitch is smaller than the first pitch and is smaller than the second pitch.

18. A manufacturing apparatus for an absorbent article according to claim 5, wherein
the predetermined pitch is smaller than the first pitch and is smaller than the second pitch.

19. A manufacturing apparatus for an absorbent article according to claim 6, wherein
the predetermined pitch is smaller than the first pitch and is smaller than the second pitch.

20. A manufacturing apparatus for an absorbent article according to claim 7, wherein
the predetermined pitch is smaller than the first pitch and is smaller than the second pitch.

* * * * *